(12) United States Patent
Cai et al.

(10) Patent No.: US 6,686,502 B1
(45) Date of Patent: Feb. 3, 2004

(54) COMPOUNDS AND METHODS FOR TREATMENT OF ASTHMA, ALLERGY AND INFLAMMATORY DISORDERS

(75) Inventors: Xiong Cai, Belmont, MA (US); Timothy Lewis, Marlborough, MA (US)

(73) Assignee: UCB S.A., Brussels (BE)

( * ) Notice: Subject to any disclaimer, the term of this patent is extended or adjusted under 35 U.S.C. 154(b) by 1 day.

(21) Appl. No.: 10/386,226

(22) Filed: Mar. 11, 2003

Related U.S. Application Data

(63) Continuation of application No. 10/242,346, filed on Sep. 12, 2002, which is a continuation of application No. 09/534,947, filed on Mar. 24, 2000, now Pat. No. 6,451,801.
(60) Provisional application No. 60/126,521, filed on Mar. 26, 1999.

(51) Int. Cl.$^7$ ............................................. C07C 259/04
(52) U.S. Cl. ........................................ 562/623; 564/58
(58) Field of Search ............................. 562/623; 564/58

(56) References Cited

U.S. PATENT DOCUMENTS

| | | | |
|---|---|---|---|
| 2,898,339 A | 9/1959 | Wheeler | 260/293.4 |
| 4,282,233 A | 9/1981 | Vilani et al. | 424/267 |
| 4,525,358 A | 6/1985 | Baltes et al. | 514/255 |
| 5,066,658 A | 11/1991 | Demers et al. | 514/269 |
| 5,438,062 A | 9/1995 | Ganguly | 514/290 |
| 5,616,596 A | 4/1997 | Basha et al. | 514/365 |
| 5,714,609 A | 2/1998 | Remiszewski | 546/94 |
| 6,451,801 B1 * | 9/2002 | Scannell et al. | 514/253.03 |

FOREIGN PATENT DOCUMENTS

| | | |
|---|---|---|
| EP | 0 270 818 | 6/1988 |
| FR | 2345430 | 10/1977 |
| GB | 1574822 | 9/1980 |
| WO | WO 95/10515 | 4/1995 |
| WO | WO 95/13264 | 5/1995 |
| WO | WO 98/57946 | 12/1998 |

OTHER PUBLICATIONS

Nagai et al., (1979) *Chemical and Pharmaceutical Bulletin*, vol. 27, No. 9, pp. 2056–2064.

Honrubia et al. (1997) *Chemical and Pharmaceutical Bulletin*, vol. 45, No. 5, p. 842.

Lozo et al., (1993) *Journal of Pharmaceutical Sciences*, vol. 82, No. 11, p. 1090.

* cited by examiner

*Primary Examiner*—Richard L. Raymond
(74) *Attorney, Agent, or Firm*—McDonnell Boehnen Hulbert & Berghoff

(57) ABSTRACT

The present invention provides 1,4 substituted piperazines, 1,4 substituted piperidines, and 1-substituted,4-alkylidenyl piperidines compounds. The compounds of the invention are dual acting molecules having both leukotriene inhibition properties as well as antihistaminergic properties. The compounds of the invention are useful for treating conditions in which there is likely to be a histamine and/or leukotriene component. These conditions include preferably asthma, seasonal and perennial allergic rhinitis, sinusitus, conjunctivitis, food allergy, scombroid poisoning, psoriasis, urticaria, pruritus, eczema, rheumatoid arthritis, inflammatory bowel disease, chronic obstructive pulmonary disease, thrombotic disease and otitis media. Also provided are methods of treating asthma and rhinitis by administering an effective asthma and rhinitis-relieving amount of the compounds to a subject in need thereof.

1 Claim, 9 Drawing Sheets

COMPOUNDS AND METHODS FOR TREATMENT OF ASTHMA, ALLERGY AND INFLAMMATORY DISORDERS

CROSS-REFERENCE TO RELATED APPLICATIONS

This is a continuation of application Ser. No. 10/242,346, filed Sep. 12, 2002, which is a continuation of application Ser. No. 09/534,947, filed Mar. 24, 2000, now U.S. Pat. No. 6,451,801 issued Sep. 17, 2002, which claims the benefit of U.S. Provisional Application No. 60/126,521 filed on Mar. 26, 1999.

BACKGROUND OF THE INVENTION

1. Field of the Invention

The invention relates to the field of 1,4 substituted piperazines, 1,4 substituted piperidines, and 1-substituted, 4-alkylidenyl piperidines.

2. Summary of the Related Art

Leukotrienes are potent local mediators, playing a major role in inflammatory and allergic responses including arthritis, asthma, psoriasis, and thrombotic disease. Leukotrienes are straight chain eicosanoids produced by the oxidation of arachidonic acid by lipoxygenases. Arachidonic acid is oxidized by 5-lipoxygenase and ultimately converted to leukotrienes A4, B4, C4, D4 or E4. 15-Lipoxygenase is responsible for the conversion of arachidonic acid to various biologically active metabolites including 15-hydroxy-5,8,11,13-eicosatetraenoic acid (15-HETE). Both of these mediators have been implicated in the pathogenesis of airway and allergic diseases such as asthma by contributing to bronchoconstriction, mucus secretion, and eosinophil migration. A mixture of one or more of such leukotrienes are known to be potent bronchoconstrictors. Thus, leukotrienes have been shown to play an important role in the pathology of asthma. Rigorous proof for the role of leukotrienes in asthma has been provided by several pivotal clinical trials in which orally administered 5-lipoxygenase (5-LO) inhibitors (or LTD4 receptor antagonists) produce clear therapeutic benefit in asthma patients. These benefits include reduction in the use of classic asthma therapies such as beta agonists and corticosteroids.

It is well known in the art that certain hydroxyurea- and hydroxyamide-substituted aromatic compounds can function as 5-LO inhibitors. For example, WO 92/09567 and WO 92/09566 disclose a wide variety of N-hydroxyurea and hydroxamic acid compounds as inhibitors of the lipoxygenase enzyme.

Histamine has been established to play a role in inflammation in general. Antihistamines are well established most notably for allergy control. Furthermore, histamine is believed to play a role in asthma. For example, histamine and cysteinyl leukotrienes (cLT's) are both known to be key mediators in airway tone. Clinical studies have shown that a combination therapy of a cLT receptor antagonist and an antihistamine administered to twelve asthma patients, reduced early asthmatic responses (EAR) and late asthmatic responses (LAR) to a greater extent than either single-acting agent alone (A. Roquet, et al., *Am. J. Respir Crit. Care Med*, 155, 1856 (1997)). This indicates that histamine plays a role in asthma.

It is well known that certain [bis(substituted and/or unsubstituted aryl) methyl- and methylene]-1-piperidyl compounds possess antihistaminergic activity, and numerous publications disclose such. For example, Yanni et al. (U.S. Pat. Nos. 4,810,713 and 4,950,674) disclose [[bis(aryl) methyl- or methylene-]-1-piperidinyl]alkoxy-aryl and -heteroaryl compounds for the treatment of allergic phenomena, including asthma and rhinitis. Teng et al. (U.S. Pat. No. 5,070,087) disclose [bis(aryl)methyl- and methylene]-N-[(phenoxy and phenylthio)alkyl]piperidines for countering effects of histamine in allergies.

Others have shown [bis(aryl)methyl]piperazin-1-yl compounds for use as antiasthmatics and antiallergics that inhibit leukotriene release (e.g., JP 97077754). U.S. Pat. No. 4,525,358 teaches 2-[4-(diphenylmethyl)-1-piperazinyl]-acetic acid and its amides as antiallergic, spasmolytic, and antihistamine agents. JP 7138230 discloses 4-aralkyl-1-piperazinyl-unsaturated carboxylic acid derivatives useful an antiallergic agents for the treatment of, for example, asthma and rhinitis. WO 97/23466 describes the preparation of N-diarylmethylpiperazines as analgesics.

None of the art, however, teaches, suggests, or contemplates combining the 5-LO and 15-LO inhibiting functionality of hydroxyurea moieties with the antihistaminergic properties of [bis(substituted and/or unsubstituted aryl) methyl- and methylene]-1-piperidyl or -1-piperazinyl moieties in a single entity to yield a compound possessing the dual functions as an antihistaminergic and a 5-LO/15-LO inhibitor.

SUMMARY OF THE INVENTION

The present invention provides novel compounds having dual properties, each compound possessing both lipoxygenase inhibition properties as well as antihistaminergic properties. In a preferred embodiment, each of the novel compounds of the invention functions as both a 5-LO and/or 15-LO inhibitor as well as a histamine H1 receptor antagonist.

The compounds of the invention are useful for treating conditions in which there is likely to be a histamine and/or leukotriene component. These conditions include preferably asthma, seasonal and perennial allergic rhinitis, sinusitus, conjunctivitis, food allergy, scombroid poisoning, psoriasis, urticaria, pruritus, eczema, rheumatoid arthritis, inflammatory bowel disease, chronic obstructive pulmonary disease, thrombotic disease and otitis media. Accordingly, the invention also provides pharmaceutical compositions comprising the compounds of the invention and methods of treating asthma and rhinitis with the pharmaceutical compositions.

The compounds disclosed herein can also be used as research tools to study biological pathways involving both leukotrienes and histamine and, in particular, further elucidate the role histamine plays in bronchoconstriction.

All patent applications, patents, and other publications recited herein are hereby incorporated by reference in their entirety.

DETAILED DESCRIPTION OF THE INVENTION

The Compounds

Figure 1:
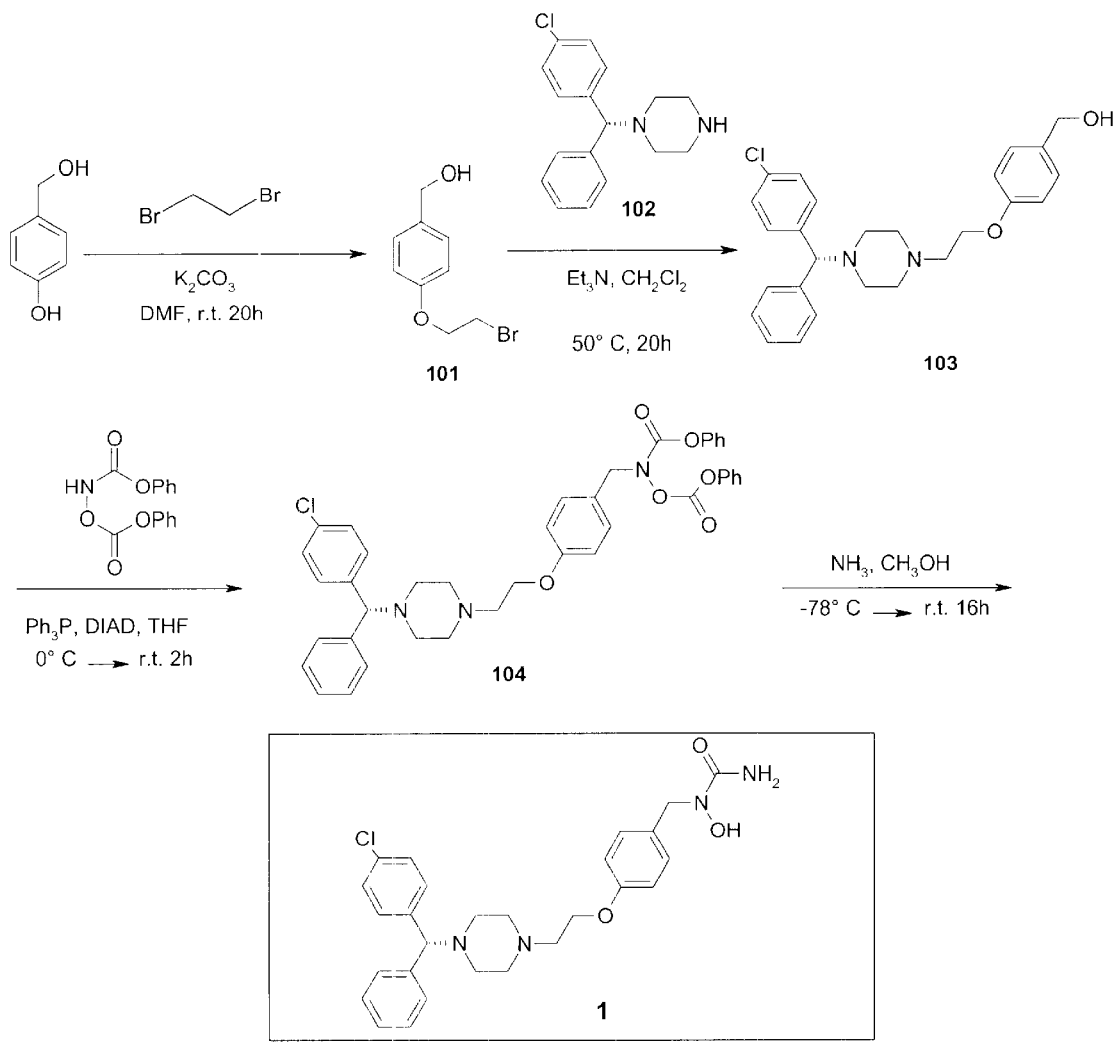
FIG. 1 displays the synthesis of compound 1.

In one aspect, the present invention comprises compounds of formula I, including geometrical isomers, enantiomers, diastereomers, racemates, and pharmaceutically acceptable salts thereof:

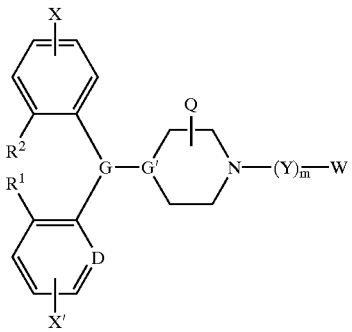

wherein:

X and X' independently are hydrogen, halo, alkyl, alkenyl, alkynyl, alkoxy, trifluoromethyl or —(Y')$_m$—W';

G and G' together form

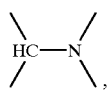

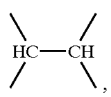

or

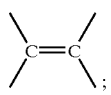

D is —CH= or =N—;

R$^1$ and R$^2$ independently are hydrogen or together are —(CH$_2$)$_n$— in which n is equal to 0, 1, 2, or 3;

m and m'are independently 0 or 1;

Y and Y' are —L$^1$— or —L$^2$—V(Z)$_t$—L$^3$— in which t is 0 or 1;

L$^1$ is alkylene, alkenylene, alkynylene, or one of the foregoing in which one or more methylenes are replaced by —O—, —S—, —S(O)—, —S(O)$_2$—, —N(Q)—, or —N(R$^3$)—;

L$^2$ is (a) alkylene, alkenylene, alkynylene, or one of the foregoing in which one or more methylenes are replaced by —O—, —S—, —S(O)—, —S(O)$_2$—, —N(Q')—, or —N(R$^4$)—, or (b) —L$^4$—C(O)—N(Q')— or —L$^4$(Q')—, or (c) a direct bond;

L$^3$ is (a) alkylene, alkenylene, alkynylene, or one of the foregoing in which one or more methylenes are replaced by —O—, —S—, —S(O)—, —S(O)$_2$—, —N(Q")—, or —N(R$^5$)—, or (b) a direct bond;

L$^4$ is (a) alkylene, alkenylene, alkynylene, or one of the foregoing in which one or more methylenes are replaced by —O—, —S—, —S(O)—, —S(O)$_2$—, —N(Q")—, or —N(R$^5$)—, or (b) a direct bond;

V is (a) a divalent arene, a divalent heteroarene, or a divalent saturated heterocycle when t is 0, or (b) a trivalent arene or trivalent heteroarene when t is 1;

Q, Q', and Q" independently are hydrogen, —AC(O)OR$^6$, or —AC(O)NR$^6$R$^7$;

W and W' independently are —N(OM)C(O)N(R$^8$)R$^9$, —N(R$^8$)C(O)N(OM)R$^9$, —N(OM)C(O)R$^8$, —C(O)NR$^8$R$^9$, or —C(O)OR$^8$, provided that at least one of W and W' is —N(OM)C(O)N(R$^8$)R$^9$, —N(R$^8$)C(O)N(OM)R$^9$, or —N(OM)C(O)R$^8$.

Z is —A"N(OM')C(O)N(R$^{10}$)R$^{11}$, —A"N(R$^{10}$)C(O)N(OM')R$^{11}$, —A"N(OM')C(O)R$^{11}$, —A'C(O)N(OM')R$^{11}$, —A'C(O)NR$^{10}$R$^{11}$, —A'C(O)OR$^{10}$, halo, CH$_3$, NR$^3$R$^4$, NR$^3$C(O)R$^4$, NO$_2$, CN, CF$_3$, S(O)$_2$NR$^3$R$^4$, S(O)$_2$R$^3$, SR$^3$, or S(O)R$^3$.

A, A' and A" independently are a direct bond, alkylene, alkenylene, alkynylene, yloalkylaryl, yloarylalkyl, or diyloalkylarene or one of the foregoing in which one or more methylenes are replaced by —O—, —NH', —S—, —S(O)—, or —S(O)$_2$— and/or one or more methylidenes are replaced by =N—;

M and M' independently are hydrogen, a pharmaceutically acceptable cation, or a metabolically cleavable group; and R$^3$, R$^4$, R$^5$, R$^6$, R$^7$, R$^8$, R$^9$, R$^{10}$, and R$^{11}$ are independently hydrogen, alkyl, alkenyl, alkynyl, aryl, arylalkyl, alkylaryl, alkylarylalkyl, or one of the foregoing in which one or more methylenes are replaced by —O—, —NH', —S—, —S(O)—, or —S(O)$_2$— and/or one or more methylidenes are replaced by =N—;

provided that, other than the oxygens bound to the sulfurs in —S(O)— and —S(O)$_2$—, when one or more methylenes are replaced with —O—, —NH—, —S—, —S(O)—, or —S(O)$_2$— and when one or more methylidenes are replaced with =N', such replacement does not result in two heteroatoms being covalently bound to each other;

and further provided that when m is 0, W is not —C(O)NR$^8$R$^9$, or —C(O)OR$^8$, and further provided that in the substituent —AC(O)OR$_6$, R$_6$ cannot be hydrogen when A is a direct bond.

Preferably, compounds of the present invention are those having formula I':

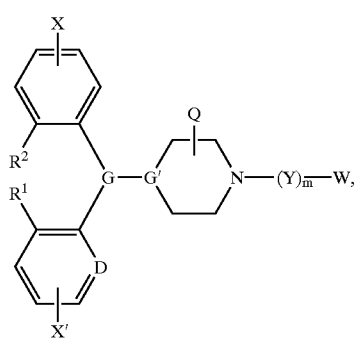

and the geometrical isomers, enantiomers, diastereomers, and pharmaceutically acceptable salts thereof, wherein each of the variables is as defined above, except that:

X and X' independently are hydrogen, halo, alkyl, alkenyl, alkynyl, alkoxy, or trifluoromethyl; and W is —N(OM)C(O)N(R$^8$)R$^9$, —N(R$^8$)C(O)N(OM)R$^9$, or —N(OM)C(O)R$^8$.

In another preferred embodiment, the compounds of the present invention are given by formula I":

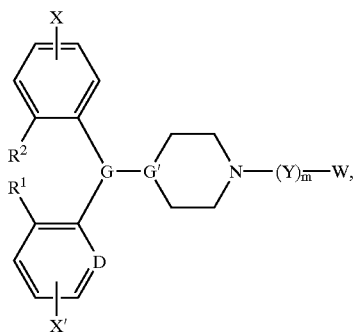

and the geometrical isomers, enantiomers, diastereomers, and pharmaceutically acceptable salts thereof, wherein each of the variables is as defined above.

In other preferred embodiments, compounds of formula I are represented by the following formulas, II and III:

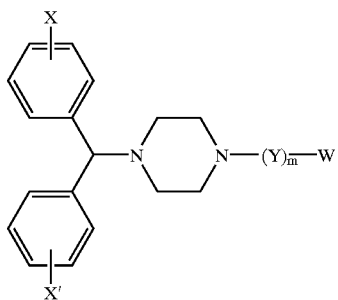

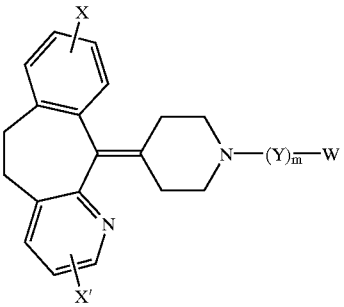

and the geometrical isomers, enantiomers, diastereomers, and pharmaceutically acceptable salts thereof, wherein each of the variables is as defined above.

More preferred embodiments of the compounds of formula II and III and the geometrical isomers, enantiomers, diastereomers, and pharmaceutically acceptable salts thereof, are those wherein each of the variables is as defined above except that:

1. X is —Cl, X' is hydrogen, m is 1 and W is —N(OH)C(O)NH$_2$;
2. X is —Cl, X' is hydrogen, m is 1, Y is —L$^1$—, wherein L$^1$ is alkynylene, yloalkoxy, or yloalkoxyalkyl;
3. X is —Cl, X' is hydrogen, m is 1, Y is —L$^2$—V(Z)$_t$—L$^3$—, t is 0, V is 1,4-phenylene or 1,3-phenylene, L$^2$ is yloalkoxy, and L$^3$ is alkylene, alkenylene, or alkynylene;
4. X is —Cl, X' is hydrogen, m is 1, Y is —L$^2$—V(Z)$_t$—L$^3$—, t is 0, V is 2,5-furylene, L$^2$ is alkylene, and L$^3$ is alkylene, alkenylene, or alkynylene; or
5. X is —Cl, X' is hydrogen, m is 1, Y is —L$^2$—V(Z)$_t$—L$^3$—, t is 1, L$^2$ is yloalkoxy, V is trivalent heteroarene, Z is —A'C(O)NR$^{10}$R$^{11}$ or —A'—C(O)OR$^{10}$ and W is —N(OH)C(O)NH$_2$.
6. X and X' are F, m is 1, Y is —L$^2$—V(Z)$_t$—L$^3$—, t is 0, V is 1,4-phenylene or 1,3-phenylene, L$^2$ is yloalkoxy, and L$^3$ is alkylene, alkenylene, or alkynylene;

Compounds of the invention include those shown in TABLE I as follows:

| CPD # | Structure | Stereo-Chem[1] | Salt | Melt. Temp | MS Obs Mass | LogP | Name |
|---|---|---|---|---|---|---|---|
| 1 | Chiral | CR | | | | 3.07 | N-{[4-(2-{4-[(1R)(4-chlorophenyl)phenlymethyl]piperazinyl}ethoxy)phenyl][methyl]amino-N-hydroxyamide |
| 2 | Chiral | CR | | | | 2.72 | N-{[4-(2-{4-[(1R)(4-chlorophenyl)phenylmethyl]piperazinyl}ethoxy)phenyl][methyl]aminocarbonylamino aminooate |
| 3 | Chiral | CR | | | | 3.62 | N-{[4-(3-{4-[(1R)(4-chlorophenyl)phenylmethyl]piperazinyl}prop-1-ynyl)phenyl][methyl]amino-N-hydroxyamide |

| CPD # | Structure | Stereo-Chem[1] | Salt | Melt. Temp | MS Obs Mass | LogP | Name |
|---|---|---|---|---|---|---|---|
| 4 | Chiral | CR | | | | 3.27 | N-{[4-(3-{4-[(1R)(4-chlorophenyl)phenyl]methyl]piperazinyl}prop-1-ynyl)phenyl]methyl}aminocarbonylamino aminooate |
| 5 | Chiral | CR | | | | 3.18 | N-{[3-(2-{4-[(1R)(4-chlorophenyl)phenyl]methyl]piperazinyl}ethoxy)phenyl]methyl}amino-N-hydroxyamide |
| 6 | Chiral | CR | | | | 2.82 | N-{[3-(2-{4-[(1R)(4-chlorophenyl)phenyl]methyl]piperazinyl}ethoxy)phenyl]methyl}aminocarbonylamino aminooate |

-continued

| CPD # | Structure | Stereo-Chem[1] | Salt | Melt. Temp | MS Obs Mass | LogP | Name |
|---|---|---|---|---|---|---|---|
| 7 | Chiral | CR | | | | 3.08 | N-{[2-(2-{4-[(1R)(4-chlorophenyl)phenylmethyl]piperazinyl}ethoxy)phenyl]methyl}amino-N-hydroxyamide |
| 8 | Chiral | CR | | | | 3.62 | N-{[3-(3-{4-[(1R)(4-chlorophenyl)phenylmethyl]piperazinyl}prop-1-ynyl)phenyl]methyl}amino-N-hydroxyamide |
| 9 | Chiral | CR | | | | 1.76 | N-(4-{4-[(1R)(4-chlorophenyl)phenylmethyl]piperazinyl}but-2-ynyl)amino-N-hydroxyamide |

-continued

| CPD # | Structure | Stereo-Chem[1] | Salt | Melt. Temp | MS Obs Mass | LogP | Name |
|---|---|---|---|---|---|---|---|
| 10 | 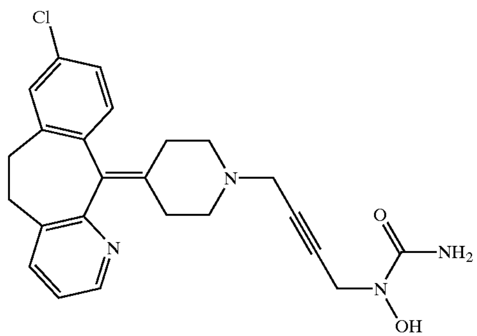 | | | | | 3.65 | amino-N-{4-[4-(8-chloro[5,6-dihydro benzo[f]pyridino[2,3-b]][7]annulen-11-ylidene])piperidyl]but-2-ynyl}-N-hydroxyamide |
| 11 | 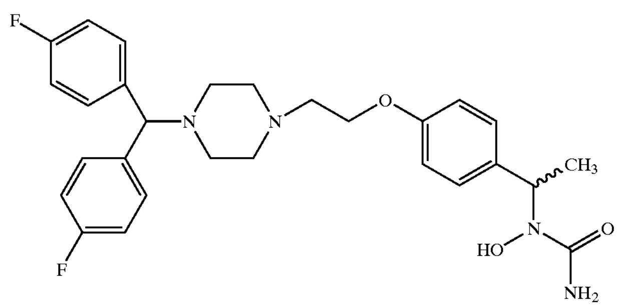 | R | | | | 3.18 | amino-N-{[4-(2-{4-[bis(4-fluorophenyl) methyl]piperazinyl]ethoxy)phenyl] ethyl}-N-hydroxyamide |
| 12 | 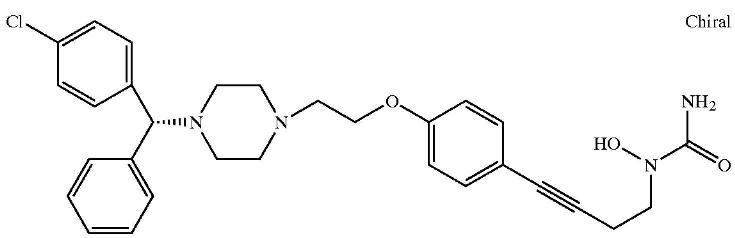 | CR Chiral | | | 533.3 | 4.19 | N-{4-[4-(2-{4-[(1R)(4-chlorophenyl) phenylmethyl]piperazinyl]ethoxy) phenyl]but-3-ynyl}amino-N-hydroxyamide |

-continued

| CPD # | Structure | Stereo-Chem[1] | Salt | Melt. Temp | MS Obs Mass | LogP | Name |
|---|---|---|---|---|---|---|---|
| 13 | Chiral | CR | | | | 3.98 | N-{[4-(3-{4-[(1R)(4-chlorophenyl)phenyl]methyl]piperazinyl}propyl)phenyl]methyl}amino-N-hydroxyamide |
| 14 | 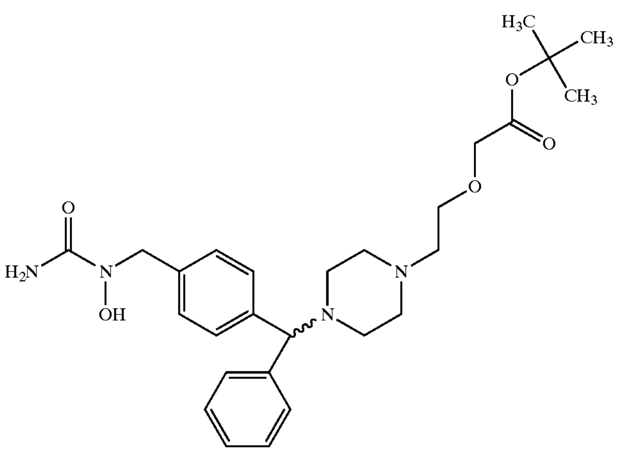 | R | | | | 1.65 | tert-butyl2-{2-[4-({4-[(aminohydroxycarbonyl)amino]methyl]phenyl}phenylmethyl)piperazinyl]ethoxy}acetate |

-continued

| CPD # | Structure | Stereo-Chem[1] | Salt | Melt. Temp | MS Obs Mass | LogP | Name |
|---|---|---|---|---|---|---|---|
| 15 | 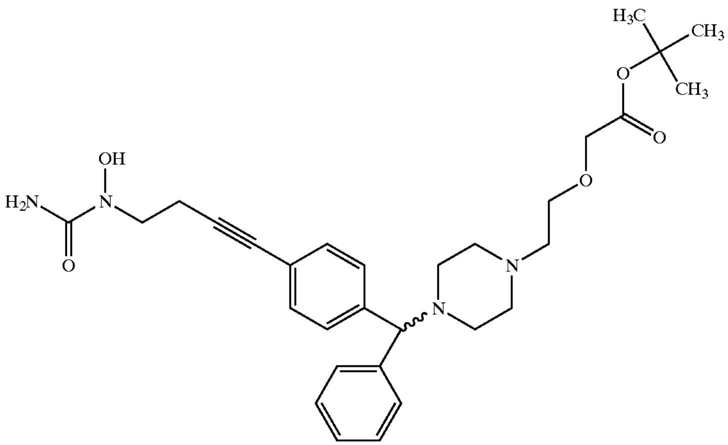 | R | | | | 2.77 | tert-butyl2-{2-[4-({4-[4-(aminohydroxycarbonyl)amino]but-1-ynyl]phenyl}phenylmethyl)piperazinyl]ethoxy}acetate |
| 16 | 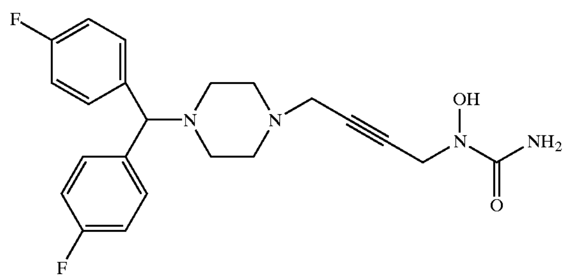 | Chiral | | | | 1.33 | amino-N-(4-{4-[bis(4-fluorophenyl)methyl]piperazinyl}but-2-ynyl)-N-hydroxyamide |
| 17 | 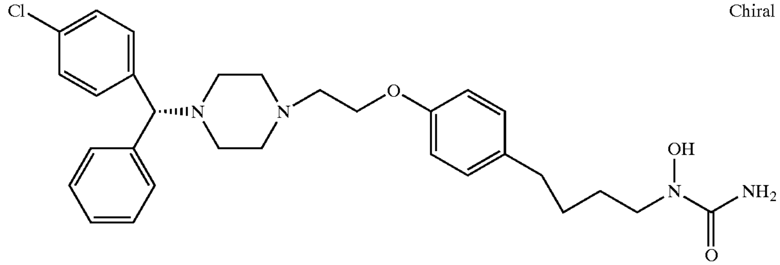 | CR | | 148-150 | 536.64 | 4.55 | N-{4-[4-(2-{4-[(1R)(4-chlorophenyl)phenylmethyl]piperazinyl}ethoxy)phenyl]butyl}amino-N-hydroxyamide |

-continued

| CPD # | Structure | Stereo-Chem[1] | Salt | Melt. Temp | MS Obs Mass | LogP | Name |
|---|---|---|---|---|---|---|---|
| 18 | 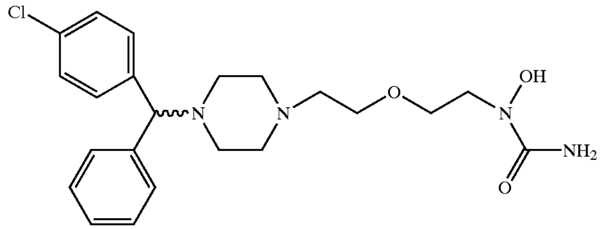 | R | | | | 1.05 | amino-N-[2-(2-{4-[(4-chlorophenyl)phenylmethyl]piperazinyl}ethoxy)ethyl]-N-hydroxyamide |
| 19 | 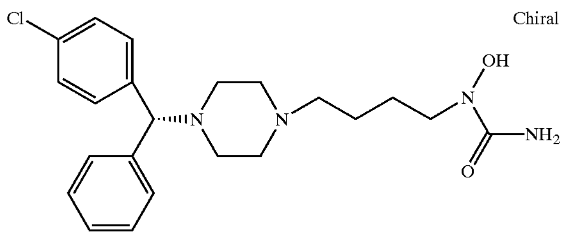 | CR Chiral | | | | 2.37 | N-(4-{4-[(1R)(4-chlorophenyl)phenylmethyl]piperazinyl}butyl)amino-N-hydroxyamide |
| 20 | 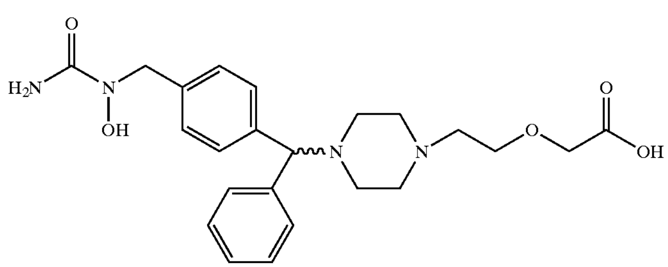 | R | 2 HCl | | | -0.04 | 2-{2-[4-({4-[(aminohydroxycarbonyl amino)methyl]phenyl}methyl)piperazinyl]ethoxy}acetic acid |

-continued

| CPD # | Structure | Stereo-Chem[1] | Salt | Melt. Temp | MS Obs Mass | LogP | Name |
|---|---|---|---|---|---|---|---|
| 21 | 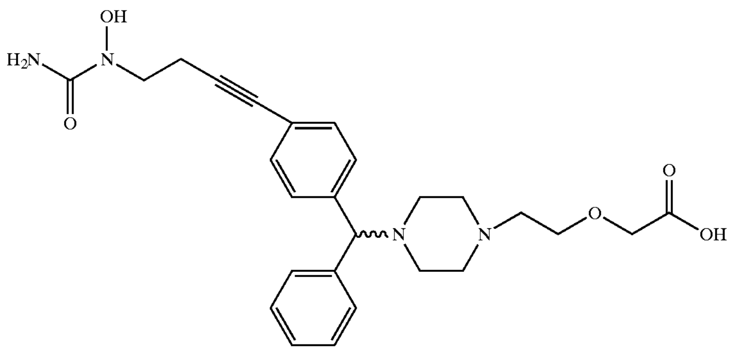 | R | 2 HCl | | | 1.08 | 2-{2-[4-({4-[4-(aminohydroxycarbonyl amino)but-1-ynyl]phenyl}phenyl methyl)piperazinyl]ethoxy}aceticacid |
| 22 | 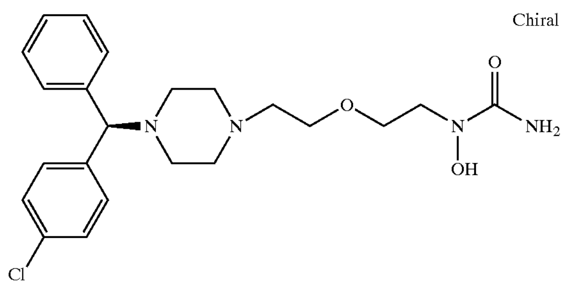 | CR | | | | 1.34 | N-[2-(2-{4-[(1R)(4-chlorophenyl) phenylmethyl]piperazinyl}ethoxy)ethyl] amino-N-hydroxyamide |

| CPD # | Structure | Stereo-Chem | Salt | Melt. Temp | MS Obs Mass | LogP | Name |
|---|---|---|---|---|---|---|---|
| 23 | Chiral | CR | | | 533.2 | 4.19 | N-{4-[3-(2-{4-[(1R)(4-chlorophenyl)phenylmethyl]piperazinyl}ethoxy)phenyl]but-3-ynyl}amino-N-hydroxyamide |
| 24 | Chiral | CR | | | 509.2 | 3.82 | N-{[3-(2-{4-[(1R)(4-chlorophenyl)phenylmethyl]piperazinyl}ethoxy)phenyl]methyl}(methyl(hydroxyamino))carboxamide |
| 25 | Chiral | Chiral S | | | | 1.34 | N-[2-(2-{4-[(1S)(4-chlorophenyl)phenylmethyl]piperazinyl}ethoxy)ethyl]amino-N-hydroxyamide |

-continued

| CPD # | Structure | Stereo-Chem[1] | Salt | Melt. Temp | MS Obs Mass | LogP | Name |
|---|---|---|---|---|---|---|---|
| 26 | Chiral | CR | | | 455 | 2.44 | N-[{5-({4-[(1R)(4-chlorophenyl)phenyl]methyl]piperazinyl}methyl)(2-furyl)]methyl}amino-N-hydroxyamide |
| 27 | Chiral | CR | | | 493.2 | 3.45 | N-{4-[5-({4-[(1R)(4-chlorophenyl)phenyl]methyl]piperazinyl}methyl)(2-furyl)]but-3-ynyl}amino-N-hydroxyamide |
| 28 | 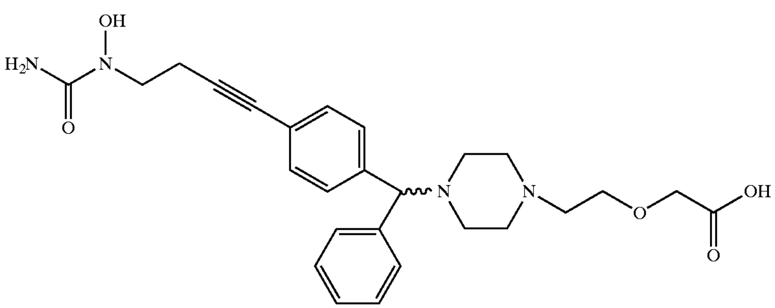 | R | 2 TFA | | 480.2 | 1.08 | 2-{2-[4-({4-[4-(aminohydroxycarbonyl amino)but-1-ynyl]phenyl}phenyl methyl)piperazinyl]ethoxy}acetic acid |

| CPD # | Structure | Stereo-Chem[1] | Salt | Melt. Temp | MS Obs Mass | LogP | Name |
|---|---|---|---|---|---|---|---|
| 29 | 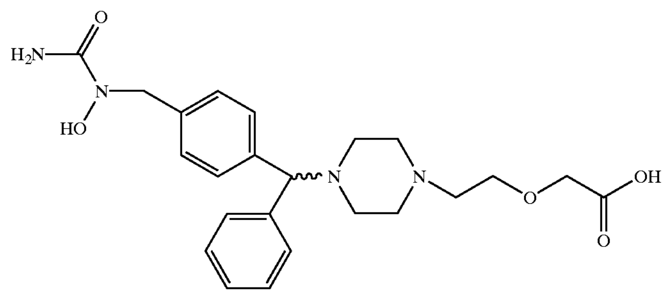 | R | 2 TFA | | 442.2 | −0.04 | 2-{2-[4-({4-[(aminohydroxycarbonyl amino)methyl]phenyl}phenylmethyl) piperazinyl]ethoxy}aceticacid |
| 30 | 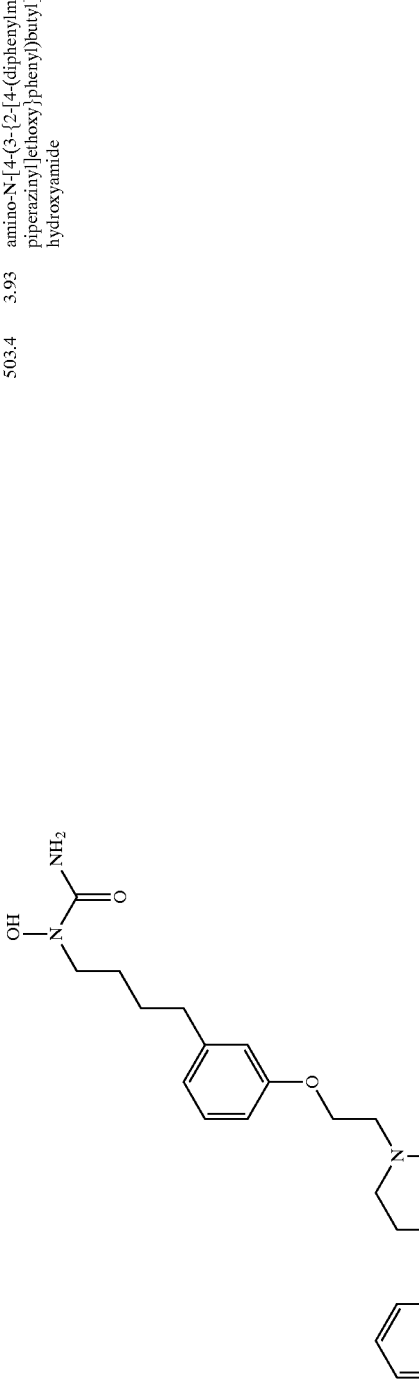 | | | | 503.4 | 3.93 | amino-N-[4-(3-{2-[4-(diphenylmethyl) piperazinyl]ethoxy}phenyl)butyl]-N-hydroxyamide |

-continued

| CPD # | Structure | Stereo-Chem[1] | Salt | Melt. Temp | MS Obs Mass | LogP | Name |
|---|---|---|---|---|---|---|---|
| 31 | 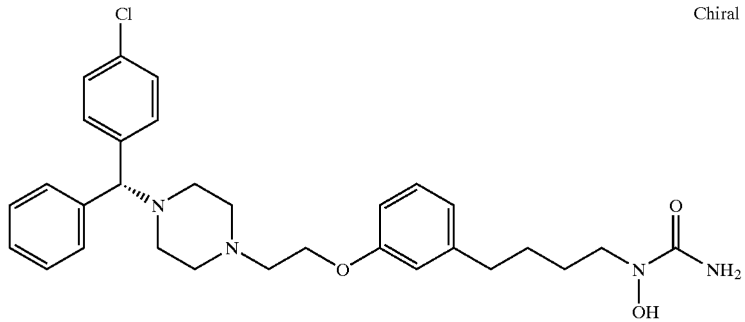 | Chiral CR | | | 537.1 | 4.64 | N-{4-[3-(2-{4-[(1R)(4-chlorophenyl)phenylmethyl]piperazinyl}ethoxy)phenyl]butyl}amino-N-hydroxyamide |
| 32 | 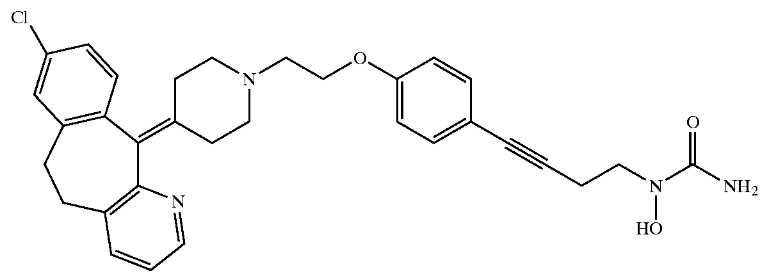 | | | | 557.14 | 6.08 | amino-N-[4-(2-[4-{8-chloro(5,6-dihydrobenzo[f]pyridino[2,3-b][7]annulen-11-ylidene))piperidyl]ethoxy}phenyl]but-3-ynyl]-N-hydroxyamide |
| 33 | 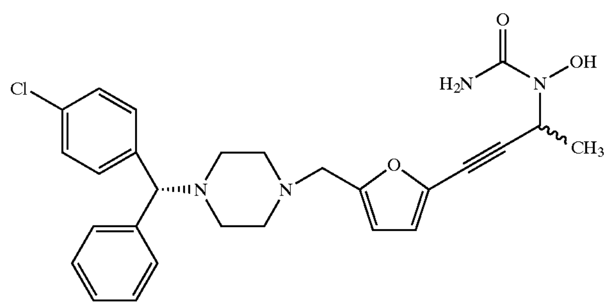 | M | | | 493.2 | 3.48 | N-{3-[5-({4-[(1R)(4-chlorophenyl)phenylmethyl]piperazinyl}methyl)(2-furyl)]-1-methylprop-2-ynyl}amino-N-hydroxyamide |

-continued

| CPD # | Structure | Stereo-Chem[1] | Salt | Melt. Temp | MS Obs Mass | LogP | Name |
|---|---|---|---|---|---|---|---|
| 34 | 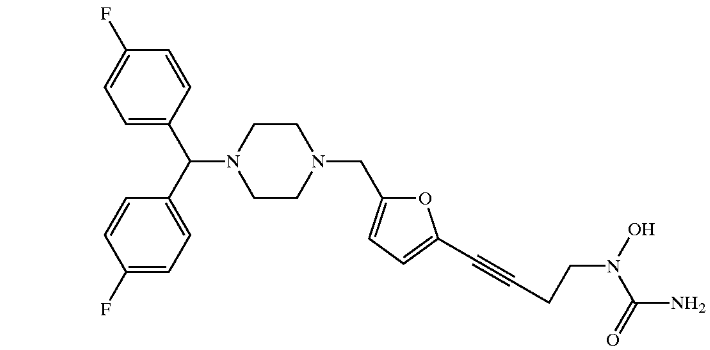 | | | | 494 | 3.03 | amino-N-{4-[5-({4-[bis(4-fluorophenyl)methyl]piperazinyl}methyl)(2-furyl)]but-3-ynyl}-N-hydroxyamide |
| 35 | 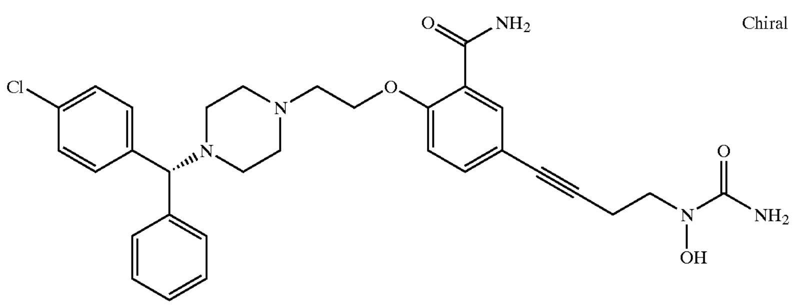 | Chiral | CR | 156–158 | 575.45 | 3.14 | 2-(2-{4-[(1R)(4-chlorophenyl)phenylmethyl]piperazinyl}ethoxy)-5-[4-(aminohydroxycarbonylamino)but-1-ynyl]benzamide |

| CPD # | Structure | Stereo-Chem[1] | Salt | Melt. Temp | MS Obs Mass | LogP | Name |
|---|---|---|---|---|---|---|---|
| 36 | Chiral | CR | | | 591.1 | 4.33 | methyl 2-(2-{4-[(1R)(4-chlorophenyl)phenylmethyl]piperazinyl}ethoxy)-5-[4-(aminohydroxycarbonylamino)but-1-ynyl]benzoate |
| 37 | Chiral | CR | | | 577.1 | 3.89 | 2-(2-{4-[(1R)(4-chlorophenyl)phenylmethyl]piperazinyl}ethoxy)-5-[4-(aminohydroxycarbonylamino)but-1-ynyl]benzoic acid |

| CPD # | Structure | Stereo-Chem[1] | Salt | Melt. Temp | MS Obs Mass | LogP | Name |
|---|---|---|---|---|---|---|---|
| 38 | 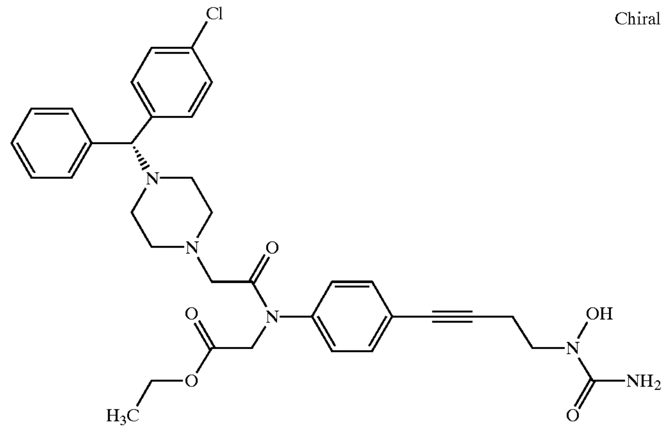 | Chiral CR | | | 616.1 | 3.64 | ethyl2-(2-{4-[(1R)(4-chlorophenyl)phenylmethyl]piperazinyl}-N-{4-[4-(aminohydroxycarbonylamino)but-1-ynyl]phenyl}acetylamino)acetate |
| 39 | 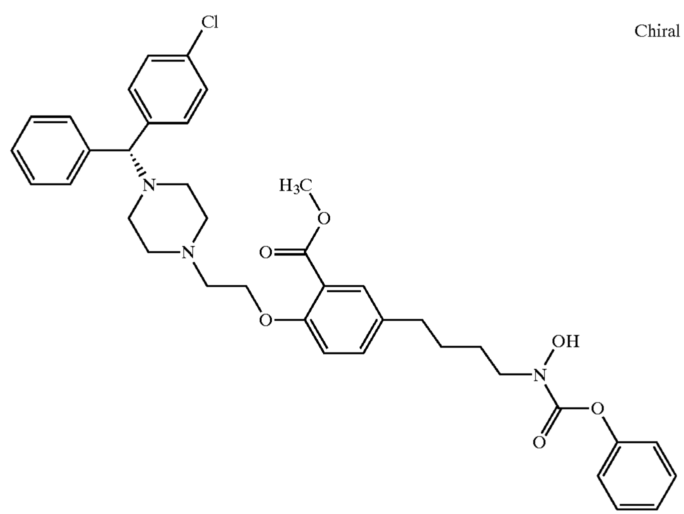 | Chiral CR | | | 672.1 | 7.37 | methyl2-(2-{4-[(R)-(4-chlorophenyl)(phenyl)methyl]-1-piperazinyl}ethoxy)-5-{4-[hydroxy(phenoxycarbonyl)amino]butyl}benzoate |

-continued

| CPD # | Structure | Stereo-Chem[1] | Salt | Melt. Temp | MS Obs Mass | LogP | Name |
|---|---|---|---|---|---|---|---|
| 40 | Chiral | CR | | | 595.2 | 4.83 | methyl 2-(2-{4-[(1R)(4-chlorophenyl)phenylmethyl]piperazinyl}ethoxy)-5-[4-(aminohydroxycarbonylamino)butyl]benzoate |
| 41 | Chiral | CR | | | 581.2 | 4.39 | 2-(2-{4-[(1R)(4-chlorophenyl)phenylmethyl]piperazinyl}ethoxy)-5-[4-(aminohydroxycarbonylamino)butyl]benzoic acid |

-continued

| CPD # | Structure | Stereo-Chem[1] | Salt | Melt. Temp | MS Obs Mass | LogP | Name |
|---|---|---|---|---|---|---|---|
| 42 | Chiral | CR | | | 580.2 | 3.64 | 2-(2-{4-[(1R)(4-chlorophenyl)phenylmethyl]piperazinyl}ethoxy)-5-[4-(aminohydroxycarbonylamino)butyl]benzamide |
| 43 | Chiral | CR | 2 HCl | | 581.2 | 4.39 | 2-(2-{4-[(1R)(4-chlorophenyl)phenylmethyl]piperazinyl}ethoxy)-5-[4-(aminohydroxycarbonylamino)butyl]benzoicacid |

-continued
| CPD # | Structure | Stereo-Chem[1] | Salt | Melt. Temp | MS Obs Mass | LogP | Name |
|---|---|---|---|---|---|---|---|
| 44 | 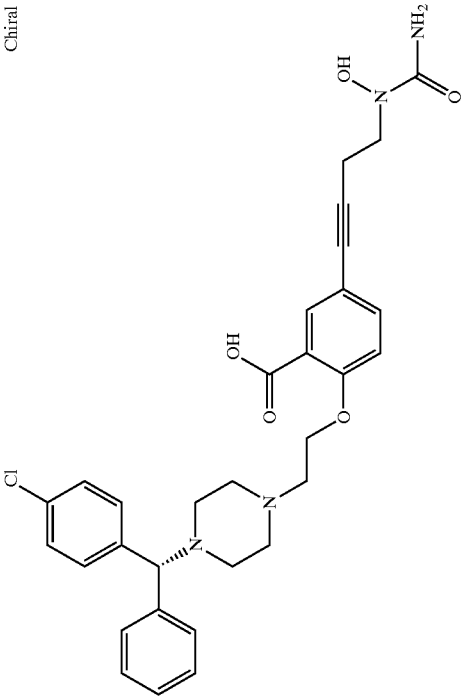 Chiral | CR | 2 HCl | | 577 | 3.89 | 2-(2-{4-[(1R)(4-chlorophenyl)phenylmethyl]piperazinyl}ethoxy)-5-[4-(aminohydroxycarbonylamino)but-1-ynyl]benzoic acid |
| 45 | 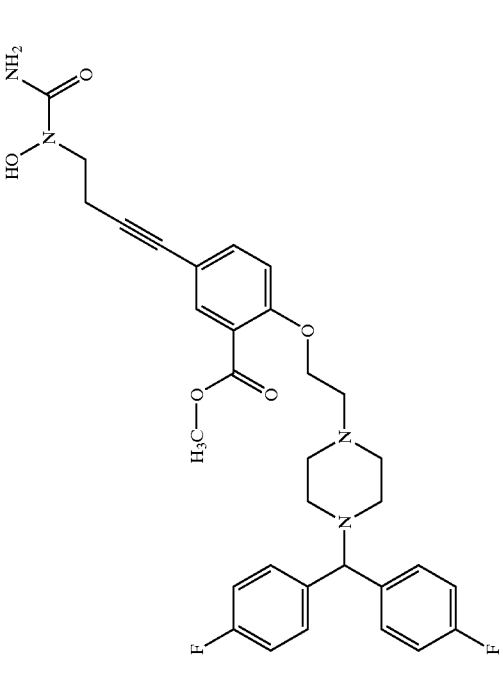 | | | | 593.3 | 3.91 | methyl 5-[4-(aminohydroxycarbonylamino)but-1-ynyl]-2-(2-{4-[bis(4-fluorophenyl)methyl]piperazinyl}ethoxy)benzoate |

| CPD # | Structure | Stereo-Chem[1] | Salt | Melt. Temp | MS Obs Mass | LogP | Name |
|---|---|---|---|---|---|---|---|
| 46 | 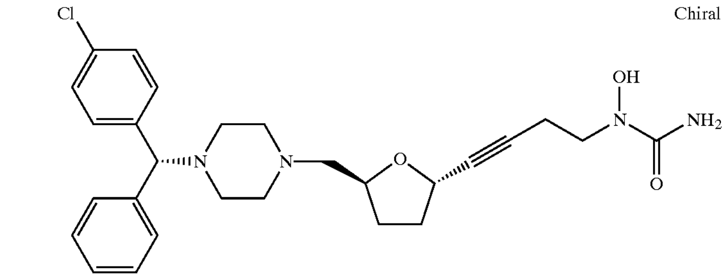 | Chiral Chiral | | | 497 | 2.75 | N-{4-[5-({4-[(1R)(4-chlorophenyl) phenylmethyl]piperazinyl}methyl)(2S, 5S)oxolan-2-yl]but-3-ynyl}amino-N-hydroxyamide |
| 47 | 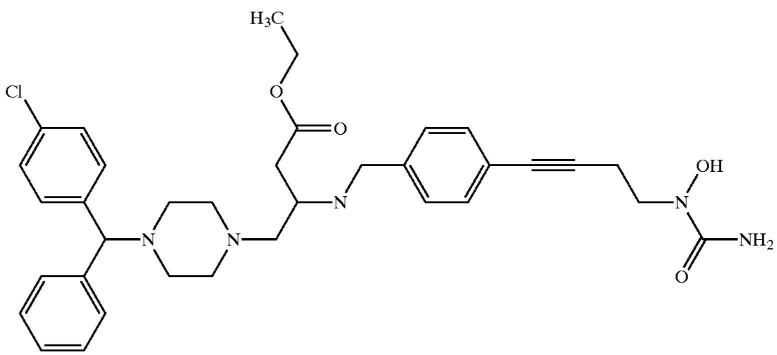 | M | | | 633 | 4.8 | ethyl 3-[({4-[4-(aminohydroxycarbonyl amino)but-1-ynyl]phenyl}methyl amino]-4-{[(4-chlorophenyl) phenylmethyl]piperazinyl}butanoate |
| 48 | 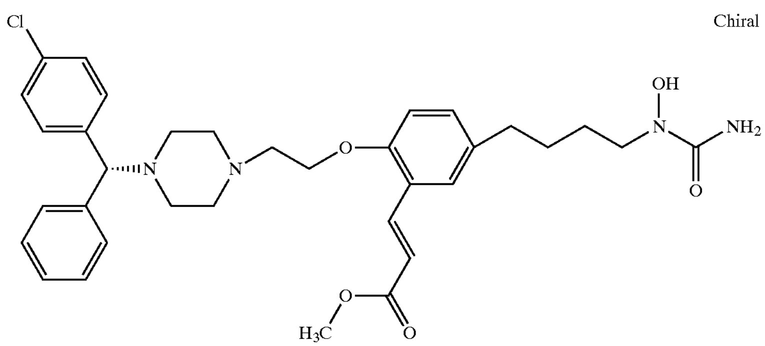 | CR Chiral | | | 621.2 | 4.97 | methyl(2E)-3-[(2-{4-[(1R)(4-chloro phenyl)phenymethyl]piperazinyl} ethoxy)-5-[4-(aminohydroxycarbonyl amino)butyl]phenyl]prop-2-enoate |

| CPD # | Structure | Stereo-Chem[1] | Salt | Melt. Temp | MS Obs Mass | LogP | Name |
|---|---|---|---|---|---|---|---|
| 49 | 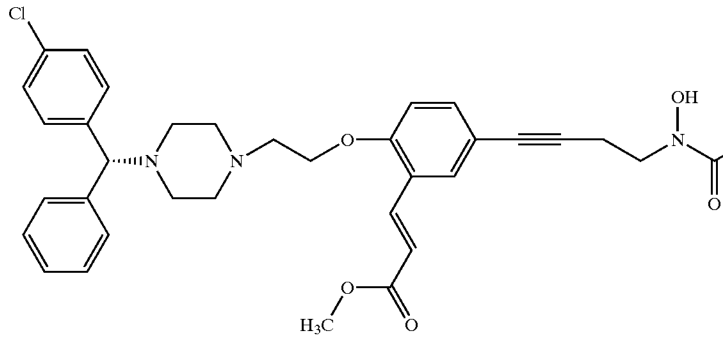 | Chiral CR | | | 617.1 | 4.63 | methyl(2E)-3-[2-(2-{4-[(1R)(4-chloro phenyl)phenylmethyl]piperazinyl]ethoxy)-5-[4-(aminohydroxycarbonyl amino)but-1-ynyl]phenyl]prop-2-enoate |
| 50 | 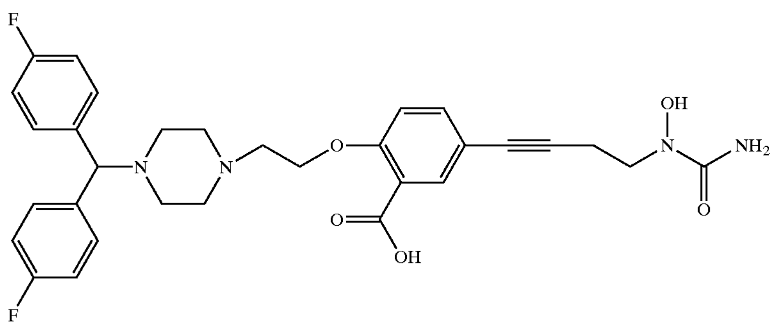 | | 2 HCl | | 579 | 3.47 | 5-[4-(aminohydroxycarbonylamino)but-1-ynyl]-2-(2-{4-[bis(4-fluorophenyl) methyl]piperazinyl}ethoxy)benzoic acid |
| 51 | 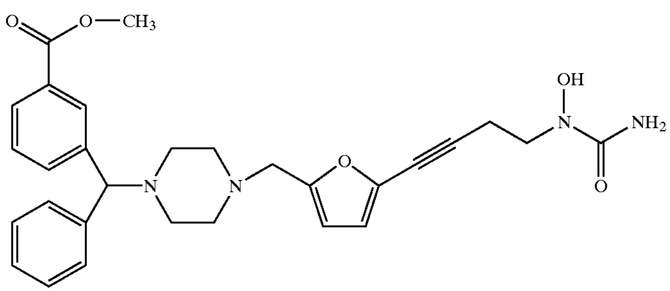 | R | | | 517.1 | 2.94 | methyl3-[[4-({5-[4-(aminohydroxy carbonylamino)but-1-ynyl][(2-furyl)} methyl)piperazinyl]phenylmethyl}] benzoate |

-continued

| CPD # | Structure | Stereo-Chem[1] | Salt | Melt. Temp | MS Obs Mass | LogP | Name |
|---|---|---|---|---|---|---|---|
| 52 | 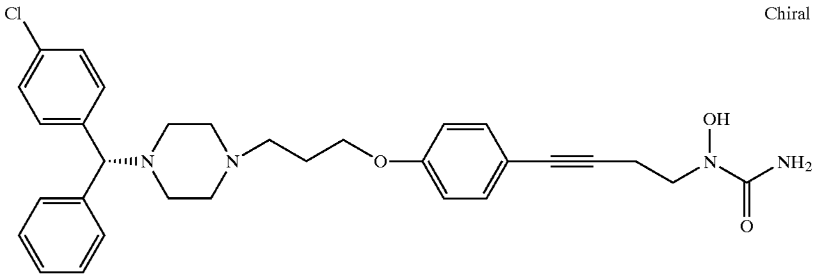 | Chiral CR | | | 547.07 | 4.54 | N-{4-[4-(3-{4-[(1R)(4-chlorophenyl)phenylmethyl]piperazinyl}propoxy)phenyl]but-3-ynyl}amino-N-hydroxyamide |
| 53 | 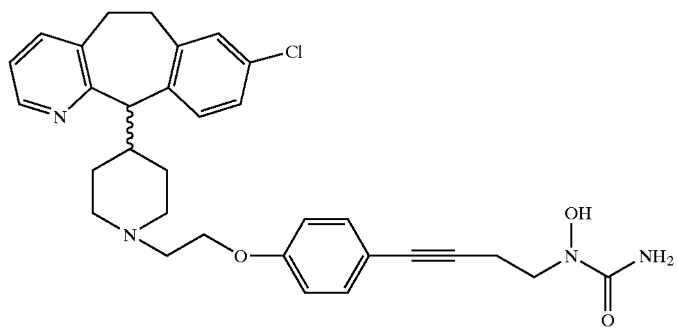 | R | | | 559.1 | 5.42 | amino-N-[4-(4-{2-[4-(8-chloro(5,6,11-trihydrobenzo[b]pyridino[3,2-f][7]annulen-11-yl))piperidyl]ethoxy}phenyl)but-3-ynyl]-N-hydroxyamide |
| 54 | 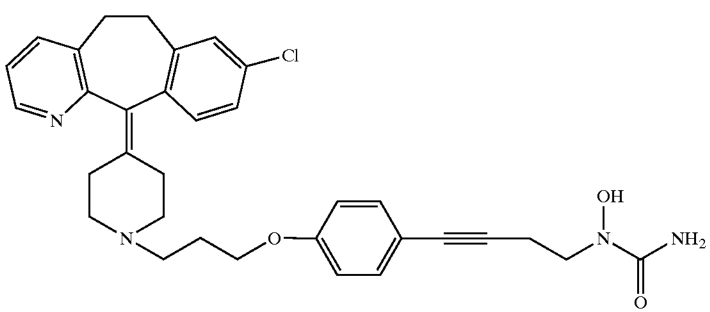 | | | | 571.14 | 6.44 | amino-N-[4-(4-{3-[4-(8-chloro(5,6-dihydrobenzo[f]pyridino[2,3-b][7]annulen-11-ylidene))piperidyl]propoxy}phenyl)but-3-ynyl]-N-hydroxyamide |

| CPD # | Structure | Stereo-Chem[1] | Salt | Melt. Temp | MS Obs Mass | LogP | Name |
|---|---|---|---|---|---|---|---|
| 55 | Chiral | CR | 2 HCl | | 603.2 | 4.19 | (2E)-3-[2-(2-(4-[(1R)(4-chlorophenyl)phenylmethyl]piperazinyl)ethoxy)-5-[4-(aminohydroxycarbonylamino)but-1-ynyl]phenyl]prop-2-enoicacid |
| 56 | Chiral | CR | | | 602 | 3.44 | N-{4-[3-((1E)-2-carbamoylvinyl)-4-(2-{4-[(1R)(4-chlorophenyl)phenylmethyl]piperazinyl}ethoxy)phenyl]but-3-ynyl}amino-N-hydroxyamide |

-continued

| CPD # | Structure | Stereo-Chem[1] | Salt | Melt. Temp | MS Obs Mass | LogP | Name |
|---|---|---|---|---|---|---|---|
| 57 | 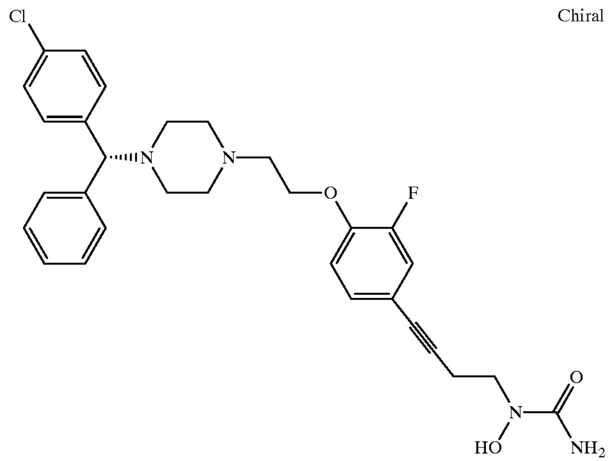 | Chiral CR | | | 551.64 | 4.35 | N-{4-[4-(2-{4-[(1R)(4-chlorophenyl)phenylmethyl]piperazinyl]ethoxy)-3-fluorophenyl]but-3-ynyl}amino-N-hydroxyamide |
| 58 | 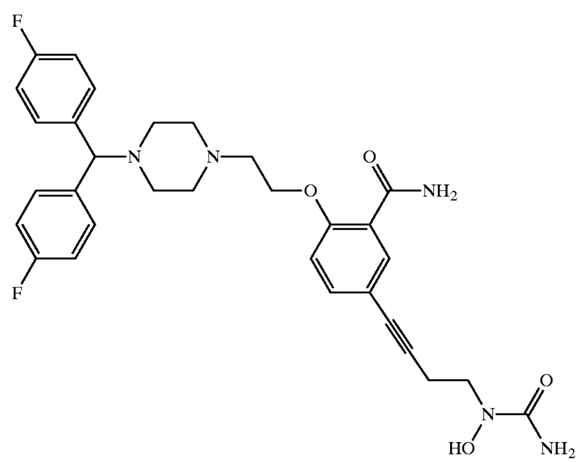 | | | | 578.02 | 2.71 | 5-[4-(aminohydroxycarbonylamino)but-1-ynyl]-2-(2-{4-[bis(4-fluorophenyl)methyl]piperazinyl}ethoxy)benzamide |

| CPD # | Structure | Stereo-Chem[1] | Salt | Melt. Temp | MS Obs Mass | LogP | Name |
|---|---|---|---|---|---|---|---|
| 59 | 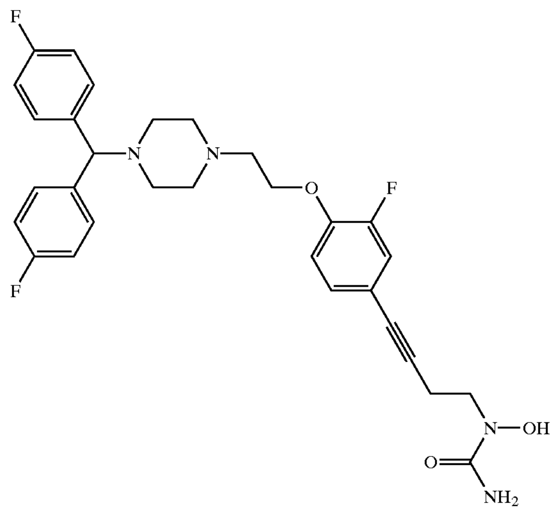 | | | | 552.96 | 3.92 | amino-N-{4-[4-(2-{4-[bis(4-fluorophenyl)methyl]piperazinyl}ethoxy)-3-fluorophenyl]but-3-ynyl}-N-hydroxyamide |
| 60 | 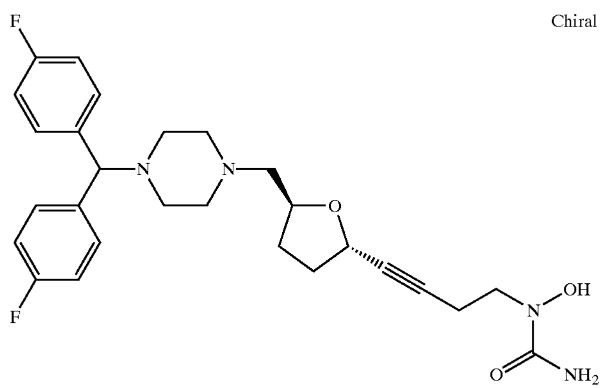 | Chiral Trans | | | 499 | 2.33 | N-{4-[(2S,5S)-5-({4-[bis(4-fluorophenyl)methyl]piperazinyl}methyl)oxolan-2-yl]but-3-ynyl}amino-N-hydroxyamide |

| CPD # | Structure | Stereo-Chem[1] | Salt | Melt. Temp | MS Obs Mass | LogP | Name |
|---|---|---|---|---|---|---|---|
| 61 | 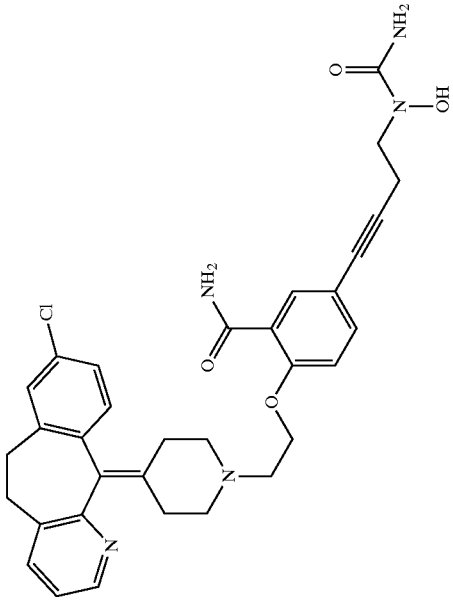 | | | | 599.82 | 5.03 | 5-[4-(aminohydroxycarbonylamino)but-1-ynyl]-2-{2-[4-(8-chloro(5,6-dihydrobenzo[f]pyridino[2,3-b][7]annulen-11-ylidene))piperidyl]ethoxy}benzamide |
| 62 | 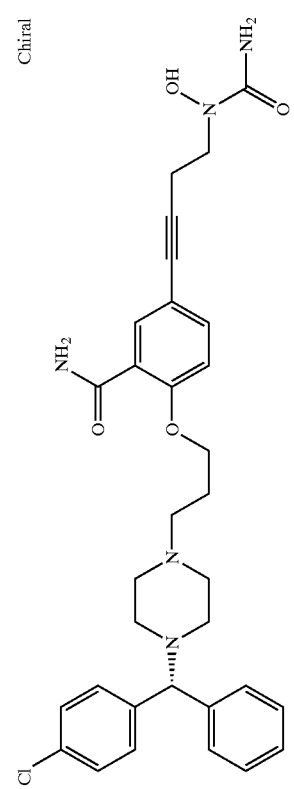 | Chiral CR | | 153–155 | 589.21 | 3.49 | 2-(3-{4-[(1R)(4-chlorophenyl)phenylmethyl]piperazinyl}propoxy)-5-[4-(aminohydroxycarbonylamino)but-1-ynyl]benzamide |

| CPD # | Structure | Stereo-Chem[1] | Salt | Melt. Temp | MS Obs Mass | LogP | Name |
|---|---|---|---|---|---|---|---|
| 63 | Chiral | CR | | | 590.06 | 3.65 | 2-(2-{4-[(1R)(4-chlorophenyl)phenylmethyl]piperazinyl}ethoxy)-5-[5-(aminohydroxycarbonylamino)pent-1-ynyl]benzamide |
| 64 | Chiral | CR | 2 HCl | 208 | 576.2 | 3.14 | 2-(2-{4-[(1R)(4-chlorophenyl)phenylmethyl]piperazinyl}ethoxy)-5-[4-(aminohydroxycarbonylamino)but-1-ynyl]benzamide |

-continued
| CPD # | Structure | Stereo-Chem[1] | Salt | Melt. Temp | MS Obs Mass | LogP | Name |
|---|---|---|---|---|---|---|---|
| 65 | 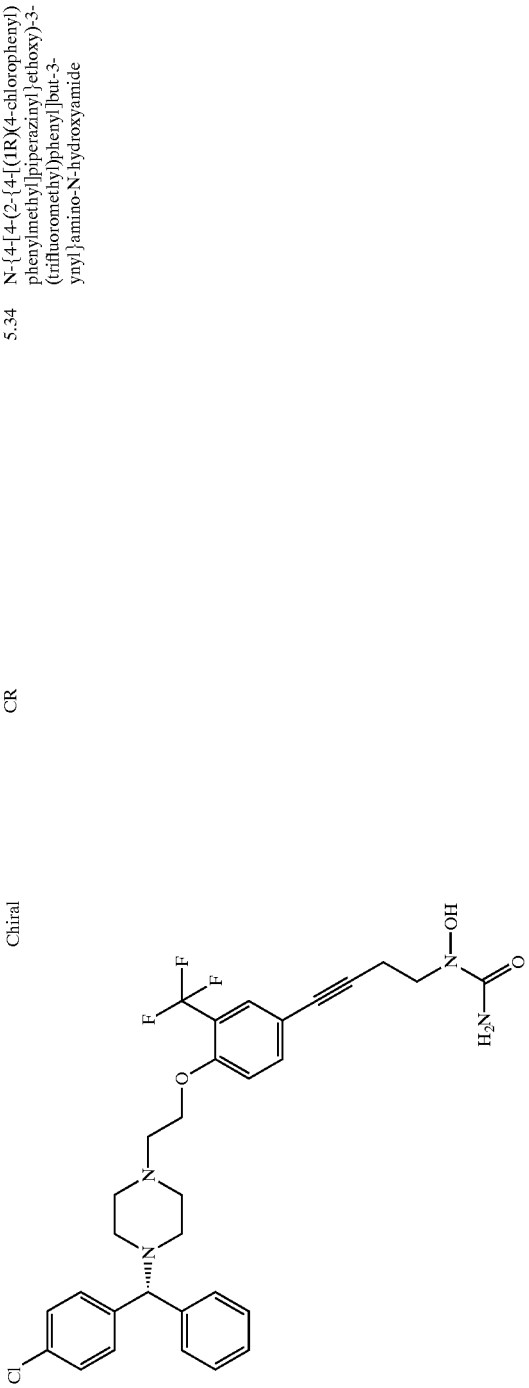 Chiral | CR | | | | 5.34 | N-{4-[4-(2-{4-[(1R)(4-chlorophenyl)phenylmethyl]piperazinyl}ethoxy)-3-(trifluoromethyl)phenyl]but-3-ynyl}amino-N-hydroxyamide |

| CPD # | Structure | Stereo-Chem[1] | Salt | Melt. Temp | MS Obs Mass | LogP | Name |
|---|---|---|---|---|---|---|---|
| 66 | 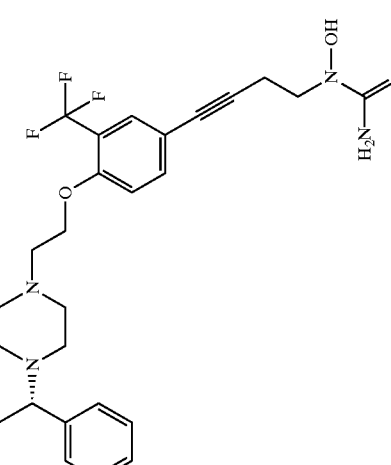 | CR | 2 HCl | | 600.36 | 5.34 | N-{4-[4-(2-{4-[(1R)(4-chlorophenyl)phenylmethyl]piperazinyl}ethoxy)-3-(trifluoromethyl)phenyl]but-3-ynyl}amino-N-hydroxyamide |
| 67 | 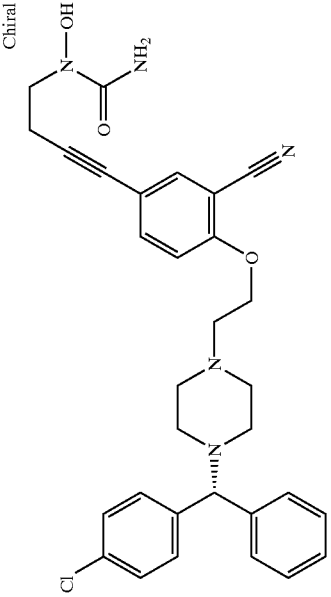 | CR | | | 557.5 | 4.1 | N-{4-[4-(2-{4-[(1R)(4-chlorophenyl)phenylmethyl]piperazinyl]ethoxy)-3-cyanophenyl]but-3-ynyl}amino-N-hydroxyamide |

-continued

| CPD # | Structure | Stereo-Chem[1] | Salt | Melt. Temp | MS Obs Mass | LogP | Name |
|---|---|---|---|---|---|---|---|
| 68 | 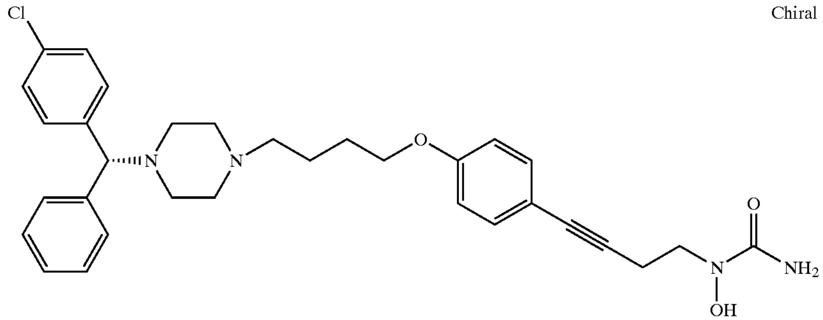 | Chiral CR | | | 560.59 | 5.05 | N-{4-[4-(4-{4-[(1R)(4-chlorophenyl)phenylmethyl]piperazinyl]butoxy}phenyl)but-3-ynyl}amino-N-hydroxyamide |
| 69 | 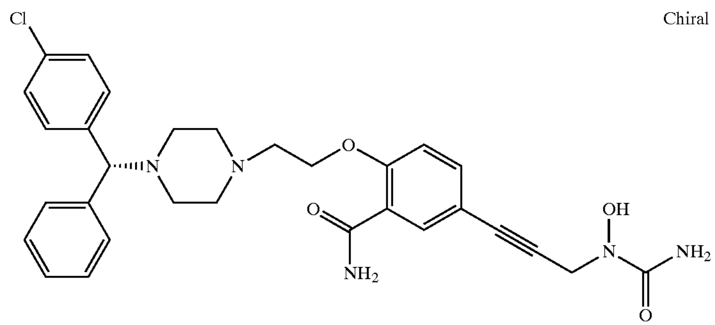 | Chiral CR | | | 561.57 | 2.63 | 2-(2-{4-[(1R)(4-chlorophenyl)phenylmethyl]piperazinyl}ethoxy)-5-[3-(aminohydroxycarbonylamino)prop-1-ynyl]benzamide |
| 70 | 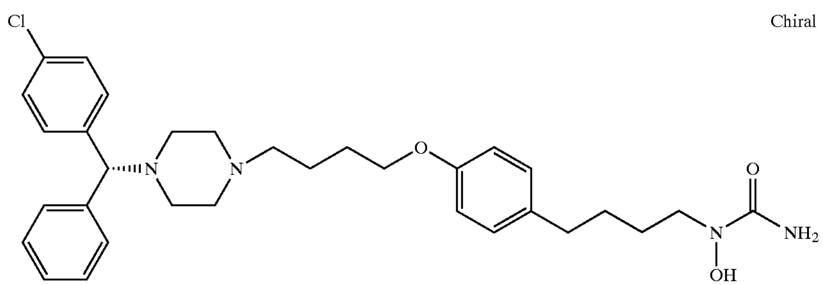 | Chiral CR | | | 564.56 | 5.41 | N-{4-[4-(4-{4-[(1R)(4-chlorophenyl)phenylmethyl]piperazinyl]butoxy}phenyl)butyl}amino-N-hydroxyamide |

-continued

| CPD # | Structure | Stereo-Chem[1] | Salt | Melt. Temp | MS Obs Mass | LogP | Name |
|---|---|---|---|---|---|---|---|
| 71 | 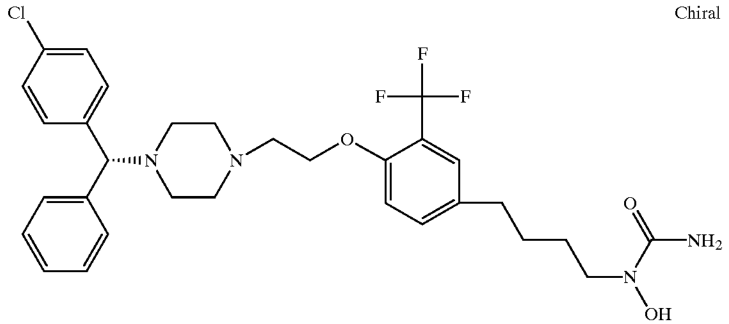 | Chiral CR | | | 604.56 | 5.84 | N-{4-[4-(2-{4-[(1S)(4-chlorophenyl)phenylmethyl]piperazinyl]ethoxy)-3-(trifluoromethyl)phenyl]butyl}amino-N-hydroxyamide |
| 72 | 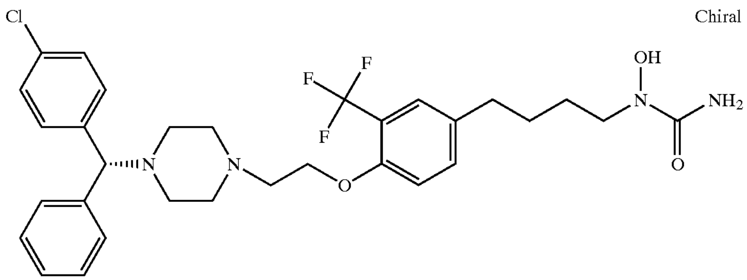 | Chiral CR | 2 HCl | | 604.44 | 5.84 | N-{4-[4-(2-{4-[(1R)(4-chlorophenyl)phenylmethyl]piperazinyl]ethoxy)-3-(trifluoromethyl)phenyl]butyl}amino-N-hydroxyamide |
| 73 | 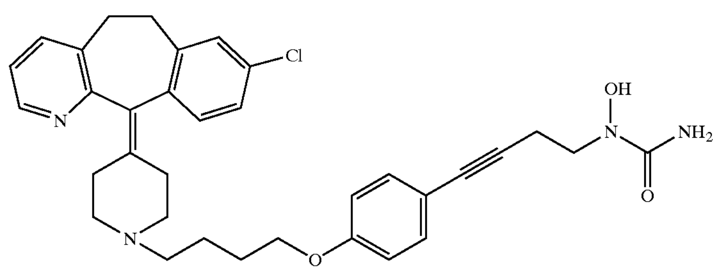 | | | | | 6.95 | amino-N-[4-(4-{4-[4-(8-chloro(5,6-dihydrobenzo[f]]pyridino[2,3-b]][7]annulen-11-ylidene))piperidyl]butoxy}phenyl)but-3-ynyl]-N-hydroxyamide |

| CPD # | Structure | Stereo-Chem[1] | Salt | Melt. Temp | MS Obs Mass | LogP | Name |
|---|---|---|---|---|---|---|---|
| 74 | 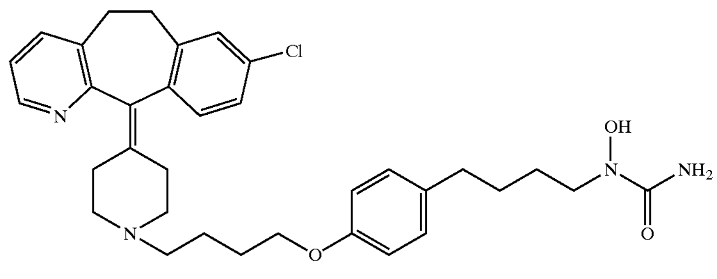 | | | | | 7.31 | amino-N-[4-{4-[4-(8-chloro(5,6-dihydrobenzo[f]pyridino[2,3-b][7]annulen-11-ylidene)piperidyl]butoxy}phenyl]-N-hydroxyamide |
| 75 | 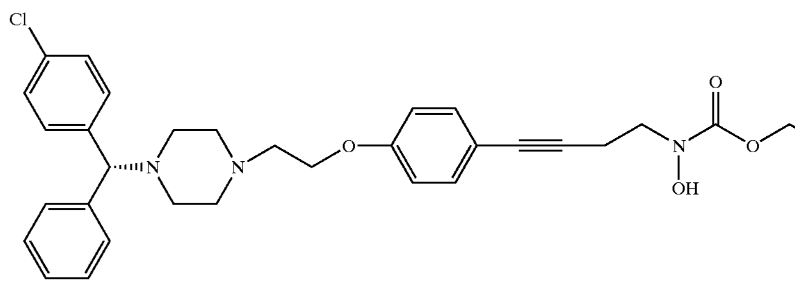 | Chiral CR | | | 561.57 | 5.4 | N-{4-[4-(2-{4-[(1R)(4-chlorophenyl)phenylmethyl]piperazinyl}ethoxy)phenyl]but-3-ynyl}-N-hydroxycarboxamide |
| 76 | 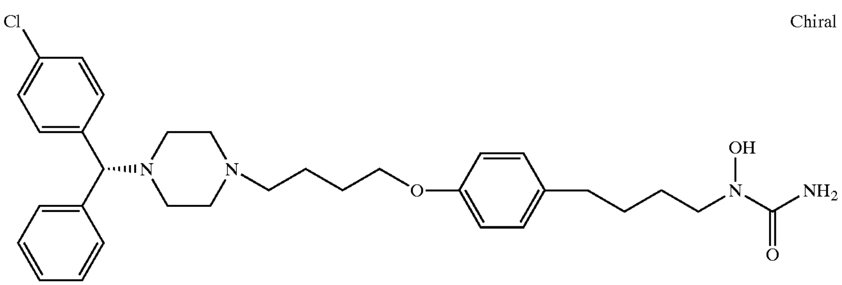 | Chiral CR | 2 HCl | 121-123 | 564.64 | 5.41 | N-{4-[4-(4-{4-[(1R)(4-chlorophenyl)phenylmethyl]piperazinyl}butoxy)phenyl]butyl}amino-N-hydroxyamide |

| CPD # | Structure | Stereo-Chem[1] | Salt | Melt. Temp | MS Obs Mass | LogP | Name |
|---|---|---|---|---|---|---|---|
| 77 | 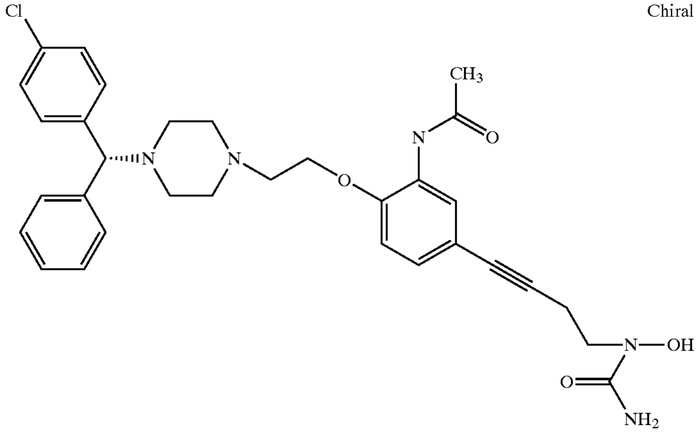 | CR Chiral | | 90–95 | 589.45 | 3.19 | N-[2-(2-{4-[(1R)(4-chlorophenyl)phenylmethyl]piperazinyl}ethoxy)-5-[4-(aminohydroxycarbonylamino)but-1-ynyl]phenyl]acetamide |
| 78 | 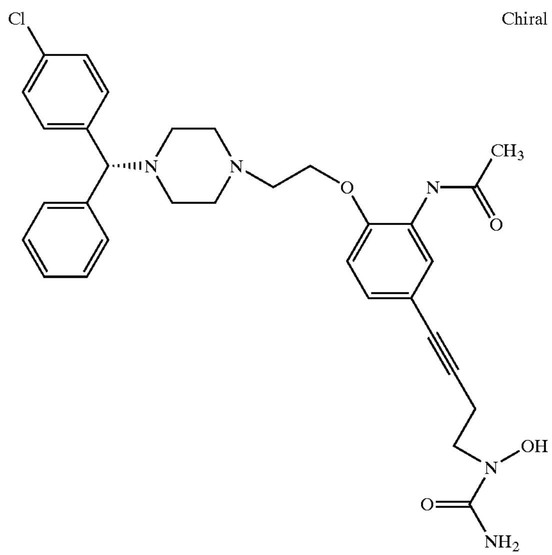 | CR Chiral | 2 HCl | 400 | 589.7 | 3.19 | N-[2-(2-{4-[(1R)(4-chlorophenyl)phenylmethyl]piperazinyl}ethoxy)-5-[4-(aminohydroxycarbonylamino)but-1-ynyl]phenyl]acetamide |

| CPD # | Structure | Stereo-Chem[1] | Salt | Melt. Temp | MS Obs Mass | LogP | Name |
|---|---|---|---|---|---|---|---|
| 79 | 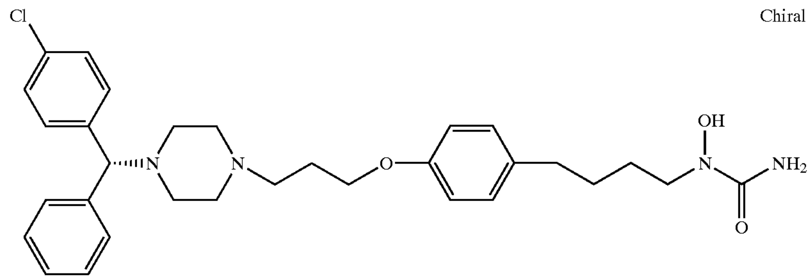 | Chiral CR | | 60-65 | 550.49 | 4.9 | N-{4-[4-(3-{4-[(1R)(4-chlorophenyl)phenylmethyl]piperazinyl}propoxy)phenyl]butyl}amino-N-hydroxyamide |
| 80 | 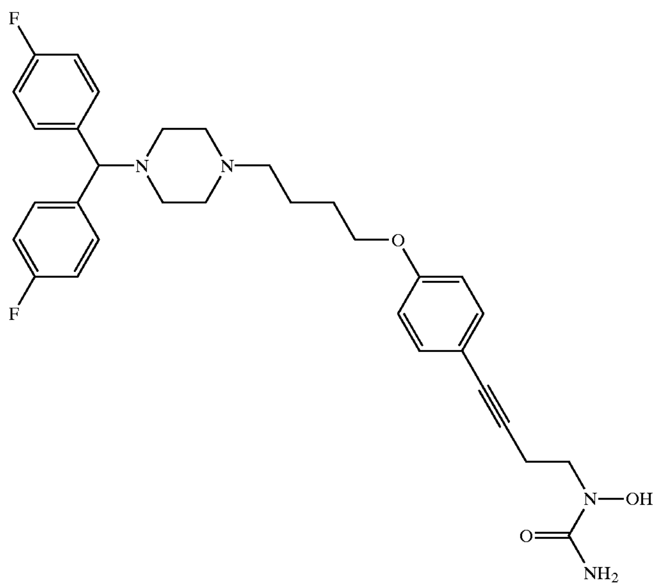 | | | 64-68 | 562.5 | 4.63 | amino-N-{4-[4-(4-{4-[bis(4-fluorophenyl)methyl]piperazinyl}butoxy)phenyl]but-3-ynyl}-N-hydroxyamide |

-continued

| CPD # | Structure | Stereo-Chem[1] | Salt | Melt. Temp | MS Obs Mass | LogP | Name |
|---|---|---|---|---|---|---|---|
| 81 | Chiral (structure) | Chiral (R, R, R) | | 42 | 496.57 | 4.39 | N-{4-[(2R)-5-({4-[(1R)(4-chlorophenyl)phenylmethyl]piperazinyl}methyl)oxolan-2-yl]but-3-ynyl}amino-N-hydroxyamide |
| 82 | (structure) | Chiral CR | | 52–90 | 536.52 | 2.75 | N-{3-[4-(3-{4-[(1R)(4-chlorophenyl)phenylmethyl]piperazinyl}propoxy)phenyl]propyl}amino-N-hydroxyamide |
| 83 | (structure) | | | 78 | 549.1 | 4.12 | amino-N-{4-[4-(3-{4-[bis(4-fluorophenyl)methyl]piperazinyl}propoxy)phenyl]but-3-ynyl}-N-hydroxyamide |

-continued
| CPD # | Structure | Stereo-Chem[1] | Salt | Melt. Temp | MS Obs Mass | LogP | Name |
|---|---|---|---|---|---|---|---|
| 84 | 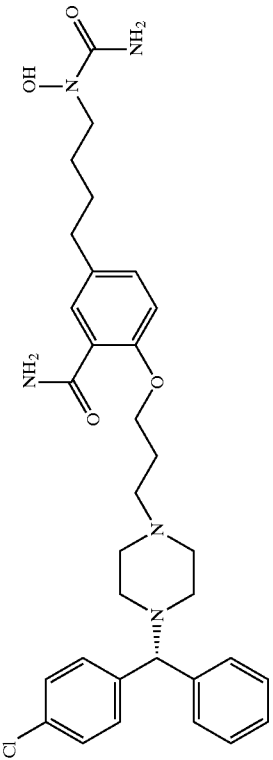 | Chiral CR | | 123–125 | 594.3 | 4 | 2-(3-{4-[(1R)(4-chlorophenyl)phenylmethyl]piperazinyl}propoxy)-5-[4-(aminohydroxycarbonylamino)butyl]benzamide |
| 85 | 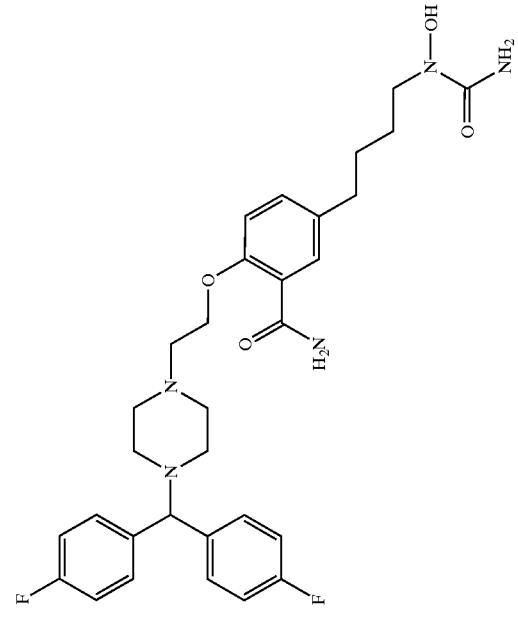 | | | 138–140 | 582.5 | 3.22 | 5-{4-[(aminocarbonyl)(hydroxy)amino]butyl}-2-(2-{4-[bis(4-fluorophenyl)methyl]-1-piperazinyl}ethoxy)benzamide |

-continued

| CPD # | Structure | Stereo-Chem[1] | Salt | Melt. Temp | MS Obs Mass | LogP | Name |
|---|---|---|---|---|---|---|---|
| 86 | 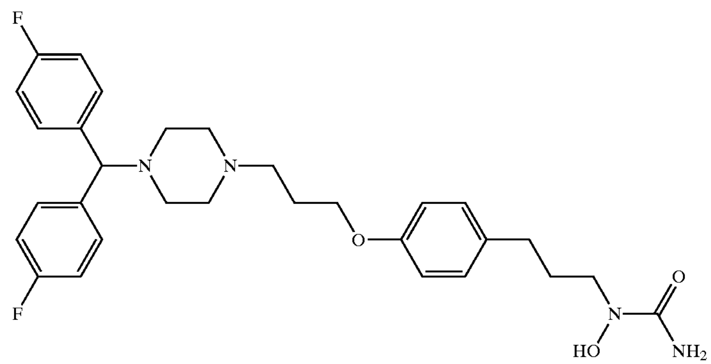 | | | 30–80 | 539.4 | 3.97 | N-{3-[4-(3-{4-[bis(4-fluorophenyl)methyl]-1-piperazinyl}propoxy)phenyl]propyl}-N-hydroxyurea |
| 87 | 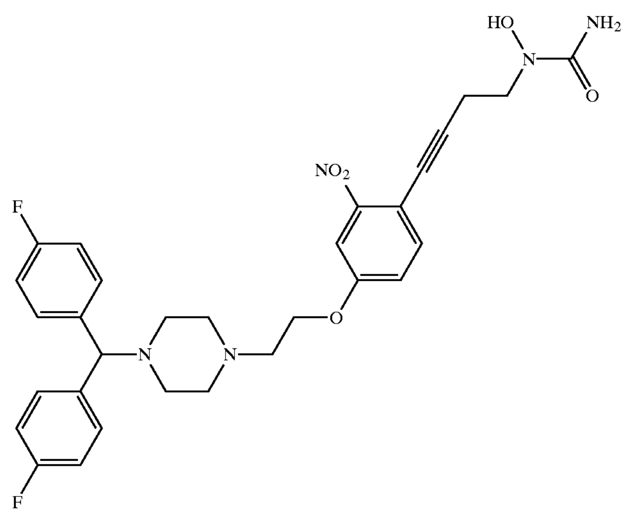 | | | 65–70 | 580.1 | 3.74 | N-{4-[4-(2-{4-[bis(4-fluorophenyl)methyl]-1-piperazinyl}ethoxy)-2-nitrophenyl[-3-butynyl]-N-hydroxyurea |

| CPD # | Structure | Stereo-Chem[1] | Salt | Melt. Temp | MS Obs Mass | LogP | Name |
|---|---|---|---|---|---|---|---|
| 88 | 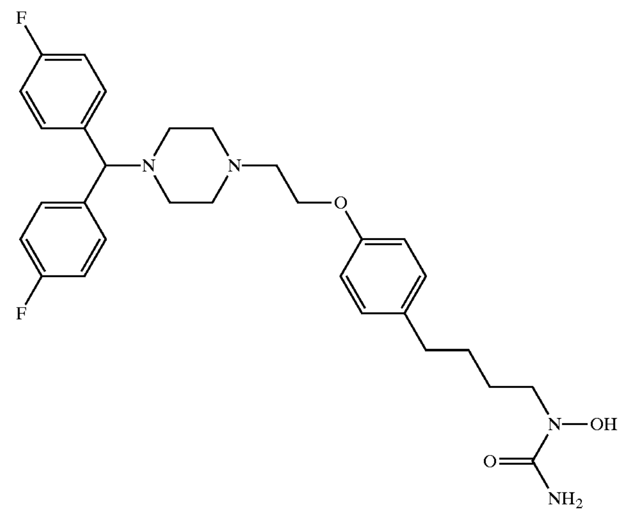 | | | 140–145 | 539.2 | 4.12 | N-{4-[4-(2-{4-[bis(4-fluorophenyl)methyl]-1-piperazinyl}ethoxy)phenyl]butyl}-N-hydroxyurea |
| 89 | 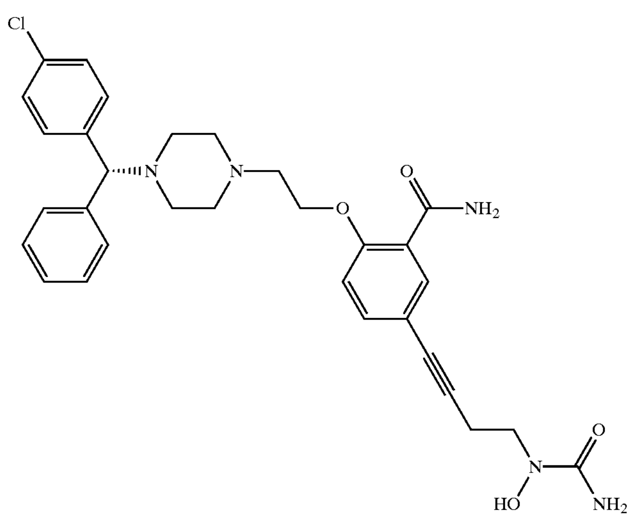 | CR | Fumarate | 162–165 | 576.2 | 3.14 | 5-{4-[(aminocarbonyl)(hydroxy)amino]-1-butynyl}-2-(2-{4-[(R)-(4-chlorophenyl)(phenyl)methyl]-1-piperazinyl}ethoxy)benzamide |

| CPD # | Structure | Stereo-Chem[1] | Salt | Melt. Temp | MS Obs Mass | LogP | Name |
|---|---|---|---|---|---|---|---|
| 90 | 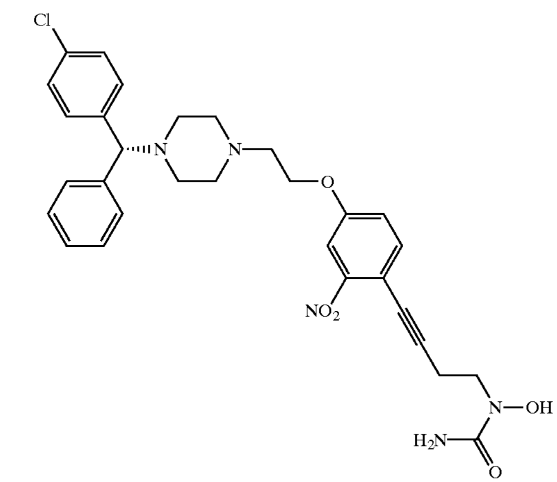 | CR | | 70–75 | 577.9 | 4.17 | N-{4-[4-(2-{4-[(R)-(4-chlorophenyl)(phenyl)methyl]-1-piperazinyl}ethoxy)-2-nitrophenyl]-3-butynyl}-N-hydroxyurea |
| 91 | 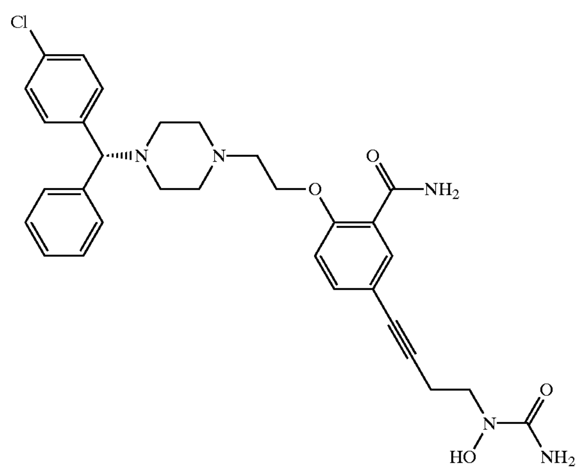 | CR | Maleate | 169–172 | 576.2 | 3.14 | 5-{4-[(aminocarbonyl)(hydroxy)amino]-1-butynyl}-2-(2-{4-[(R)-(4-chlorophenyl)(phenyl)methyl]-1-piperazinyl}ethoxy)benzamide |

| CPD # | Structure | Stereo-Chem[1] | Salt | Melt. Temp | MS Obs Mass | LogP | Name |
|---|---|---|---|---|---|---|---|
| 92 | Chiral | CR | L-tartrate | 155–158 | 576.2 | 3.14 | 5-{4-[(aminocarbonyl)(hydroxy)amino]-1-butynyl}-2-(2-{4-[(R)-(4-chlorophenyl)(phenyl)methyl]-1-piperazinyl}ethoxy)benzamide |
| 93 | Chiral | CR | Citrate | 153–156 | 576 | 3.14 | 5-{4-[(aminocarbonyl)(hydroxy)amino]-1-butynyl}-2-(2-{4-[(R)-(4-chlorophenyl)(phenyl)methyl]-1-piperazinyl}ethoxy)benzamide |

| CPD # | Structure | Stereo-Chem[1] | Salt | Melt. Temp | MS Obs Mass | LogP | Name |
|---|---|---|---|---|---|---|---|
| 94 | 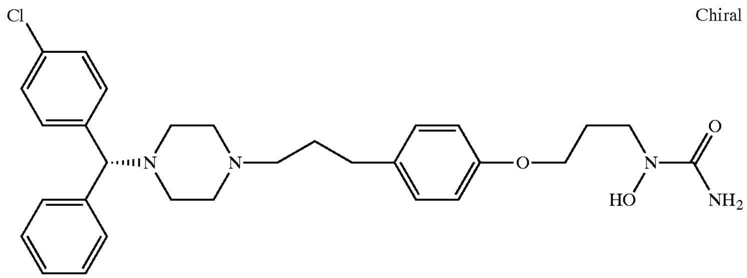 | Chiral | CR | 64–66 | 538 | 4.39 | N-{3-[4-(3-{4-[(R)-(4-chlorophenyl)(phenyl)methyl]-1-piperazinyl}propyl)phenoxy]propyl}-N-hydroxyurea |
| 95 | 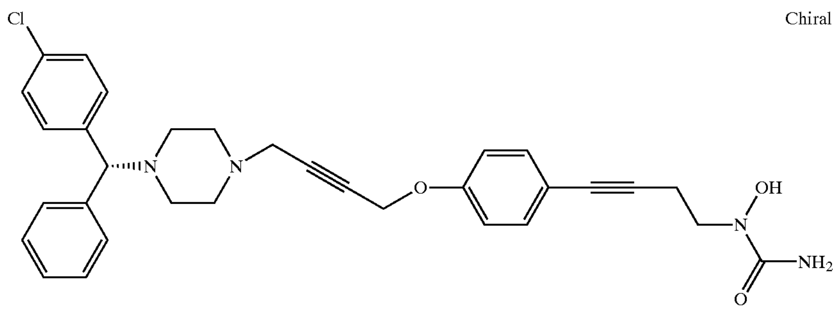 | Chiral | CR | 127–130 | 557 | 4.44 | N-(4-{4-[(4-{4-[(R)-(4-chlorophenyl)(phenyl)methyl]-1-piperazinyl}-2-butynyl)oxy]phenyl}-3-butynyl)-N-hydroxyurea |

[1] R = Racemate; CR = Chiral R; M = Mixture

Particularly preferred compounds are those listed in Table I, infra.

More preferred are compounds 1, 5, 11, 12, 13, 17, 23, 24, 31, 32, 33, 34, 35, 36, 37, 40, 41, 42, 43, 44, 45, 46, 48, 49, 50, 52, 53, 54, 55, 56, 57, 58, 59, 61, 62, 63, 64, 65, 66, 67, 68, 69, 70, 71, 72, 73, 74, 75, 76, 77, 78, 79, 80, 82, 83, 84, 85, 86, 87, 88, 89, 90, 91, 92, 93, and 94. The most preferred compounds are 17, 32, 34, 35, 46, 52 and 80.

Definitions

The following paragraphs provide definitions of the various chemical moieties that make up the compounds of the invention and are intended to apply uniformly throughout the specification and claims unless expressly stated otherwise.

The term alkyl refers to a univalent $C_1$ to $C_6$ saturated straight, branched, or cyclic alkane moiety and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The alkyl group can be optionally substituted with any appropriate group, including but not limited to $R^3$ or one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art or as taught, for example, in Greene, et al., "Protective Groups in Organic Synthesis," John Wiley and Sons, Third Edition, 1999.

The term alkoxy refers to an alkyl moiety having a terminal —O— with free a valence, e.g., $CH_3CH_2$—O—;

The term yloalkoxy is an alkoxy (as defined above) in which a hydrogen atom has been removed from the alkyl moiety to yield a divalent radical, e.g., —$CH_2CH_2O$— or —$CH(CH_3)O$—.

The term yloalkoxyalkyl refers to a divalent, dialkyl ether moiety having one free valence on each of the alkyl moieties, which alkyl moieties are the same or different, e.g., —$CH_2CH_2CH_2$—O—$CH_2$—.

The term alkylene refers to an alkyl moiety (as defined above) in which a hydrogen atom has been removed to yield a divalent radical, e.g., —$CH_2CH(CH_3)CH_2CH_2$—.

The term alkenyl refers to a univalent $C_2$–$C_6$ straight, branched, or in the case of $C_{5-6}$, cyclic hydrocarbon with at least one double bond, optionally substituted as described above.

The term alkenylene refers to an alkenyl moiety (as defined above) in which a hydrogen atom has been removed to yield a divalent radical, e.g., —$CH_2CH$=$CHCH_2$—.

The term alkynyl refers to a univalent $C_2$ to $C_6$ straight or branched hydrocarbon with at least one triple bond (optionally substituted as described above) and specifically includes acetylenyl, propynyl, and —C≡C—$CH_2$(alkyl), including —C≡C—$CH_2(CH_3)$.

The term alkynylene refers to an alkynyl moiety (as defined above) in which a hydrogen atom has been removed to yield a divalent radical, e.g., —C≡C—$CH(CH_3)$—.

The term aryl refers to a univalent phenyl (preferably), biphenyl, or napthyl. The aryl group can be optionally substituted with any suitable group, including but not limited to one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Third Edition, 1999, and preferably with halo (including but not limited to fluoro), alkoxy (including methoxy), aryloxy (including phenoxy), W, cyano, or $R^3$.

The terms arylene and divalent arene refer to an aryl moiety (as defined above) in which a hydrogen atom has been removed to yield a divalent radical, e.g., —$C_6H_4$—.

The term trivalent arene refers to an arylene moiety (as defined above) in which a hydrogen atom has been removed to yield a trivalent radical, e.g.,

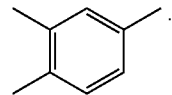

The term yloalkylaryl refers to a divalent alkyl-substituted aryl moiety in which one open valence is on the alkyl moiety and one is on the aryl moiety, e.g., —$CH_2$—$CH_2$—$C_6H_4$—.

The term yloarylalkyl refers to a divalent aryl-substituted alkyl moiety in which one open valence is on the alkyl moiety and one is on the aryl moiety, e.g., —$C_6H_4$—$CH_2$—$CH_2$—.

The term diylodialkylarene refers to a divalent, dialkyl-substituted arene in which there is one open valence on each of the alkyl moieties (which may be the same or different), e.g., —$CH_2$—$C_6H_4$—$CH_2CH_2$—.

The term heteroatom means O, S, or N.

The term heterocycle refers to a cyclic alkyl, alkenyl, or alkynyl moiety as defined above wherein one or more ring carbon atoms is replaced with a heteroatom.

The terms heteroarylene and divalent heteroarene refer to an arylene (or divalent heteroarene) that includes at least one sulfur, oxygen, or nitrogen in the aromatic ring, which can optionally be substituted as described above for the aryl groups. Non-limiting examples are, furylene, pyridylene, 1,2,4-thiadiazolylene, pyrimidylene, thienylene, isothiazolylene, imidazolylene, tetrazolylene, pyrazinylene, pyrimidylene, quinolylene, isoquinolylene, benzothienylene, isobenzofurylene, pyrazolylene, indolylene, purinylene, carbazolylene, benzimidazolylene, and isoxazolylene.

The term trivalent heteroarene refers to a heteroarylene moiety (as defined above) in which a hydrogen atom has been removed to yield a trivalent radical, e.g.,

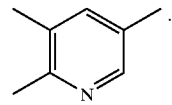

The term halo refers to chloro, fluoro, iodo, or bromo.

When a methylene of an alkyl, alkenyl, or alkynyl (or their divalent radical counterparts) is replaced by O, —NH—, —S—, —S(O)—, or —S(O)$_2$—, it may be at any suitable position in the moiety, either at the terminal or internal positions, e.g., $CH_3CH_2$—O—, $CH_3$—O—$CH_2$—, $CH_3CH_2NH$—, and $CH_3NHCH_2$—.

Open valences on the radical moieties described herein can occur on any one (or more for divalent radicals) of the atoms within the moiety. For example, the monovalent $C_3$ alkyl moiety includes both propyl and isopropyl. As another example, the divalent $C_4$ alkylene moiety includes both tetramethylene (—$CH_2(CH_2)_2CH_2$—) and ethylethylene (—$CH(CH_2CH_3)CH_2$—).

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary ammonium.

The term "metabolically cleavable group" refers to a moiety that can be cleaved in vivo from the molecule to which it is attached, and includes but is not limited to an organic or inorganic anion, a pharmaceutically acceptable cation, acyl (for example (alkyl)C(O), including acetyl, propionyl, and butyryl), alkyl, phosphate, sulfate and sulfonate, $NH_2C(O)$— or (alkyl)OC(O)—.

The term 5-lipoxygenase inhibitor refers to a compound that inhibits the enzyme at 30 $\mu$M or lower. The term 15-lipoxygenase inhibitor refers to a compound that inhibits the enzyme at 30 $\mu$M or lower.

As used herein, the term pharmaceutically acceptable salts or complexes refers to salts or complexes that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as fumaric acid, maleic acid, acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include, but are not limited to the quaternary ammonium salt of the formula —$NR^+Z^-$, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as fumarate, benzoate, succinate, acetate, glycolate, maleate, malate, citrate, tartrate, ascorbate, benzoate, cinnamoate, mandeloate, benzyloate, and diphenylacetate).

The term pharmaceutically active derivative refers to any compound that upon administration to the recipient, is capable of providing directly or indirectly, the compounds disclosed herein.

Synthetic Schemes

The synthetic schemes displayed in FIGS. 1–9 and Examples 1–7 illustrate how compounds according to the invention can be made. Those skilled in the art will be able to routinely modify and/or adapt these schemes and descriptions to synthesize any compound of the invention.

Pharmaceutical Compositions, Methods of Treatment and Administration

The compounds of the invention are useful for treating conditions in which there is likely to be a histamine and/or leukotriene component. These conditions include preferably asthma, seasonal and perennial allergic rhinitis, sinusitus, conjunctivitis, food allergy, scombroid poisoning, psoriasis, urticaria, pruritus, eczema, rheumatoid arthritis, inflammatory bowel disease, chronic obstructive pulmonary disease, thrombotic disease and otitis media. The compounds exhibit this biological activity by acting as histamine HI receptor antagonists, by inhibiting the lipoxygenase enzymes such as 5-lipoxygenase, or by exhibiting dual activity, i.e., by acting as both a histamine Hi receptor antagonist and inhibitor of lipoxygenase such as 5-lipoxygenase.

Subjects in need of treatment for a leukotriene-mediated and/or histamine-mediated condition (preferably, asthma, seasonal and perennial allergic rhinitis, sinusitus, conjunctivitis, food allergy, scombroid poisoning, psoriasis, urticaria, pruritus, eczema, rheumatoid arthritis, inflammatory bowel disease, chronic obstructive pulmonary disease, thrombotic disease and otitis media) can be treated by administering to the patient an effective amount of one or more of the above-identified compounds or a pharmaceutically acceptable derivative or salt thereof in a pharmaceutically acceptable carrier or diluent to reduce formation of oxygen radicals. The active materials can be administered by any appropriate route, for example, orally, parenterally, intravenously, intradermally, subcutaneously, intramuscularly or topically, in liquid, cream, gel or solid form, via a buccal or nasal spray, or aerosol.

The invention further concerns the use of the compounds of formula I for the manufacture of a medicament for therapeutic application. In particular, the invention concerns the use of the compounds of formula I for the manufacture of a medicament useful for treating conditions in which there is likely to be a histamine and/or leukotriene component. The invention concerns the use of the compound of formula 1 for the manufacture of a medicament useful for treating asthma, seasonal and perennial allergic rhinitis, sinusitus, conjunctivitis, food allergy, scombroid poisoning, psoriasis, urticaria, pruritus, eczema, rheumatoid arthritis, inflammatory bowel disease, chronic obstructive pulmonary disease, thrombotic disease and otitis media, and preferably asthma, seasonal and perennial allergic rhinitis.

The invention further concerns the compounds of formula I for use as medicaments. The invention concerns the compounds of formula I for use as a medicament for treating asthma, seasonal and perennial allergic rhinitis, sinusitis, conjunctivitis, food allergy, scombroid poisoning, psoriasis, urticaria, pruritus, eczema, rheumatoid arthritis, inflammatory bowel disease, chronic obstructive pulmonary disease, thrombotic disease and otitis media, and preferably asthma, seasonal and perennial allergic rhinitis.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The methods of the invention comprise administration to a mammal (preferably human) suffering from a leukotriene-mediated and/or histamine-mediated condition (preferably, asthma and rhinitis) a pharmaceutical composition according to the invention in an amount sufficient to alleviate the condition. The compound is conveniently administered in any suitable unit dosage form, including but not limited to one containing 1 to 3000 mg, preferably 5 to 500 mg of active ingredient per unit dosage form. A oral dosage of 1–500, preferably 10–250, more preferably 25–250 mg is usually convenient.

The active ingredient should be administered to achieve peak plasma concentrations of the active compound of about 0.001–30 $\mu$M, preferably about 0.01–10 $\mu$M. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterores; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement, the desired action, such as adrenergic agonists like pseudoephedrine, antibiotics, antifungals, other anti-inflammatories, or antiviral compounds.

Solutions or suspensions used for parenteral, intradermal, subcutaneous, intravenous, intramuscular or topical application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (CA) and Guilford Pharmaceuticals (Baltimore, Md.). Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidylcholine, arachadoyl phosphatidylcholine, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

The following Examples are provided for illustrative purposes only and are not intended, nor should they be construed, as limiting the invention in any manner. Those skilled in the art will appreciate that routine variations and modifications of the following Examples can be made without exceeding the spirit or scope of the invention.

EXAMPLES

Example 1

Preparation of N-{[4-(2-{4-[(1R)(4-Chlorophenyl) phenylmethyl]piperazinyl}ethoxy)phenyl]methyl}- amino-N-hydroxyamide (Compound 1, FIG. 1)
4-(2-Bromoethoxy)benzylalcohol (Compound 101)

To a solution of 4-hydroxybenzylalcohol (2.0 g, 16.11 mmol) in DMF (10 mL) was added potassium carbonate (2.67 g, 19.32 mmol). The reaction was stirred at room temperature for 30 minutes and then 1,2-dibromoethane (3.03 g, 16.13 mmol) was added. The reaction was stirred at room temperature for additional 20 hours and then quenched with water, and extracted with ethyl acetate. The organic layer was washed with water and brine, evaporated to yield an oil which was purified by flash column chromatography (silica gel, 3:1 hexane/ethyl acetate) to yield 101 (1.7 g, 45.7%): ¹H NMR (CDCl₃) δ 3.64 (t, 2H), 4.29 (t, 2H), 4.62 (s, 2H), 6.91 (d, 2H), 7.30 (d, 2H).

4-{2-[4-((1R)(4-Chlorophenyl)phenylmethyl)piperazinyl]ethoxy}benzylalcohol (Compound 103)

To a solution of 101 (205 mg, 0.89 mmol), [(1R)(4-chlorophenyl)phenylmethyl]-piperazine (102) (230 mg, 0.80 mmol) in dichloromethane (2.5 mL) was added triethylamine (122.0 mg, 1.21 mmol). The reaction was stirred at 50° C. for 20 hours. The solvent was evaporated and the residue was purified by flash column chromatography (silica gel, 3:1 hexane/ethyl acetate) to yield 103 (330 mg, 94.1%): ¹H NMR (CDCl₃) δ 2.45 (m, 4H), 2.62 (m, 4H), 2.81 (t, 2H), 4.08 (t, 2H), 4.22 (s, 1H), 4.51 (s, 2H), 6.87 (d, 2H), 7.28 (m, 6H), 7.39 (m, 5H).

N-{[4-(2-{4-[(1R)(4-Chlorophenyl)phenylmethyl]piperazinyl}ethoxy)phenyl]methyl}phenoxycarbonylaminophenoxyformate (Compound 104)

To a stirred solution of 103 (330 mg, 0.76 mmol), phenoxycarbonylaminophenoxyformate (251.6 mg, 0.92 mmol) and triphenylphosphine (225.2 mg, 0.86 mmol) in THF (8 mL) at 0° C. was added diisopropylazodicarboxylate (174.1 mg, 0.86 mmol). After addition, the reaction was warmed to room temperature and stirred at room temperature for 2 hours. The solvent was evaporated and the residue was purified by flash column chromatography (silica gel, 2:1 hexane/ethyl acetate) to give 104 (410 mg, 78.4%): ¹H NMR (CDCl₃) δ 2.47 (m, 4H), 2.65 (m, 4H), 2.84 (t, 2H), 4.12 (t, 2H), 4.23 (s, 1H), 4.95 (s, 2H), 6.92 (d, 2H), 7.20 (m, 5H), 7.26 (m, 6H), 7.40 (m, 10H).

N-{[4-(2-{4-[(1R)(4-Chlorophenyl)phenylmethyl]piperazinyl}ethoxy)phenyl]methyl}-amino-N-hydroxyamide (compound 1)

In a screw top vessel was placed a solution of 104 (410 mg, 0.59 mmol) in methanol (15 mL) and cooled to −78° C. with dry ice-acetone bath. To this vessel was added liquid NH₃ (2–3 mL) and sealed. The dry ice-acetone bath was then removed and the reaction was stirred at room temperature for 16 hours. The reaction was cooled again in a dry ice-acetone bath and the pressure released. The vessel was opened and the solvent was evaporated. Compound 1 was separated by flash column chromatography (silica gel, 19:1 CH₂Cl₂/CH₃OH) (215 mg, 73.2%): ¹H NMR (CDCl₃) δ 2.42 (m, 4H), 2.59 (m, 4H), 2.74 (t, 2H), 3.98 (t, 2H), 4.20 (s, 1H), 4.57 (s, 2H), 5.22 (bs, 2H), 6.77 (d, 2H), 7.25 (m, 6H), 7.36 (m, 5H).

Example 2

Figure 2:
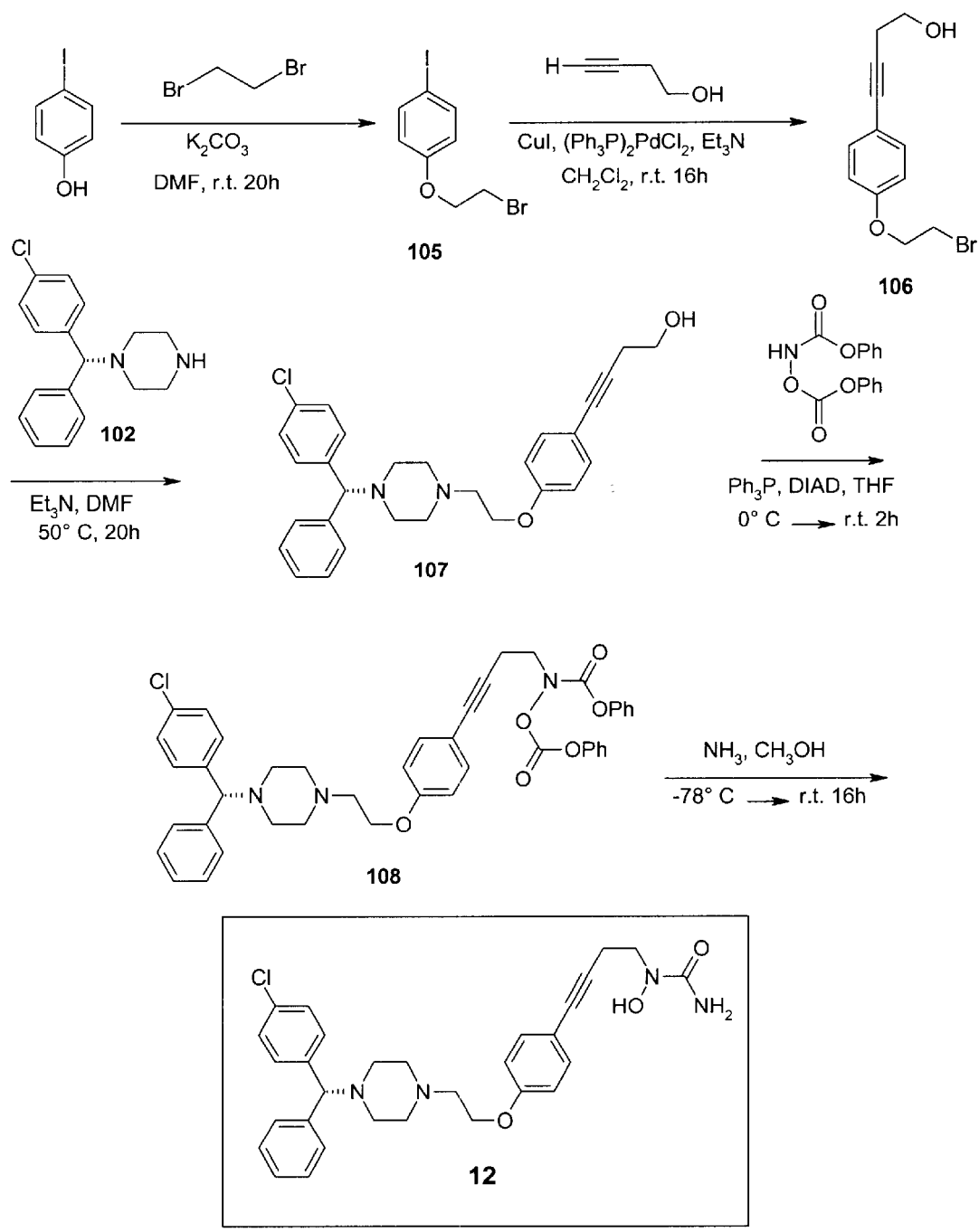
FIG. 2 displays the synthesis of compound 12.

Preparation of N-{(4-[4-(2-{4-[(1R)(4-chlorophenyl)phenylmethyl]piperazinyl}ethoxy)phenyl]but-3-ynyl}-amino-N-hydroxyamide (Compound 12, FIG. 2)

4-(2-Bromoethoxy)-1-iodobenzene (Compound 105)

To a solution of 4-iodophenol (10.0 g, 45.45 mmol) in DMF (50 mL) was added potassium carbonate (12.6 g, 91.17 mmol). The reaction was stirred at room temperature for 30 minutes and then 1,2-dibromoethane (17.07 g, 90.91 mmol) was added. The reaction was stirred at room temperature for additional 16 hours and then quenched with water and extracted with dichloromethane. The organic layer was washed with water and brine, evaporated to yield an oil which was purified by flash column chromatography (silica gel, hexane) to yield 105 (2.7 g, 18.2%): ¹H NMR (CDCl₃) δ 3.63 (t, 2H), 4.26 (t, 2H), 6.70 (d, 2H), 7.58 (d, 2H).

4-[4-(2-Bromoethoxy)phenyl]but-3-yn-1-ol (Compound 106)

To a mixture of 105 (2.7 g, 8.26 mmol), 3-butyn-1-ol (696.3 mg, 9.94 mmol), dichlorobis(triphenylphosphine)palladium(II) (1.15 g, 1.64 mmol) and cuprous iodide (317.1 mg, 1.67 mmol) was added triethylamine (45 mL). The reaction was stirred at room temperature for 16 hours. The solvent was evaporated and the residue purified by flash column chromatography (silica gel, 3:1 hexane/ethyl acetate) to yield 106 (1.3 g, 58.6%): ¹H NMR (CDCl₃) δ 2.70 (m, 4H), 3.65 (t, 2H), 3.82 (m, 2H), 4.30 (t, 2H), 6.83 (d, 2H), 7.37 (d, 2H).

4-{4-[2-(4-((1R)(4-Chlorophenyl)phenylmethyl)piperazinyl)ethoxy]phenyl}but-3-yn-1-ol (Compound 107)

To a solution of 106 (1.5 g, 5.58 mmol), [(1R)(4-chlorophenyl)phenylmethyl]piperazine (102) (1.6 g, 5.59 mmol) in DMF (15 mL) was added triethylamine (871.2 mg, 8.63 mmol). The reaction was stirred at 50° C. for 20 hours, water was added, and the reaction mixture was extracted with ethyl acetate. The organic layer was washed with water and brine, dried over magnesium sulfate, filtered and evaporated to an oil which was purified by flash column chromatography (silica gel, 1:1 hexane/ethyl acetate) to yield 107 (2.6 g, 98.1%): ¹H NMR (CDCl₃) δ 2.42 (m, 4H), 2.61 (m, 4H), 2.68 (t, 2H), 2.82 (t, 2H), 3.80 (t, 2H), 4.10 (t, 2H), 4.21 (s, 1H), 6.80 (d, 2H), 7.26 (m, 5H), 7.35 (m, 6H).

N-{4-[4-(2-(4-((1R)(4-Chlorophenyl)phenylmethyl)piperazinyl)ethoxy)phenyl]but-3-ynyl}phenoxycarbonylaminophenoxyformate (Compound 108)

To a stirred solution of 107 (1.5 g, 3.16 mmol), phenoxycarbonylaminophenoxyformate (1.05 g, 3.85 mmol) and triphenylphosphine (937.1 mg, 3.57 mmol) in THF (35 mL) at 0° C. was added diisopropylazodicarboxylate (721.4 mg, 3.57 mmol). After addition, the reaction was warmed to room temperature and stirred at room temperature for 2 hours. The solvent was evaporated and the residue was purified by flash column chromatography (silica gel, 2:1 hexane/ethyl acetate) to give 108 (1.4 g, 60.6%): ¹H NMR (CDCl₃) δ 2.44 (m, 4H), 2.62 (m, 4H), 2.82 (m, 2H), 2.91 (t, 2H), 4.10 (m, 4H), 4.21 (s, 1H), 6.80 (d, 2H), 7.18 (m, 5H), 7.30 (m, 8H), 7.37 (m, 8H).

N-{4-[4-(2-{4-[(1R)(4-Chlorophenyl)phenylmethyl]piperazinyl}ethoxy)phenyl]but-3-ynyl}-amino-N-hydroxyamide (Compound 12)

In a screw top vessel was placed a solution of 108 (1.4 g, 1.92 mmol) in methanol (50 mL) and cooled to −78° C. with dry ice-acetone bath. To this vessel was added liquid NH₃ (6 mL) and sealed. The dry ice-acetone bath was then removed and the reaction was stirred at room temperature for 16 hours. The reaction was cooled again in a dry ice-acetone bath and the pressure released. The vessel was opened and the solvent evaporated. Compound 12 was separated by flash column chromatography (silica gel, 19:1 CH₂Cl₂/CH₃OH) (580 mg, 56.9%): ¹H NMR (CDCl₃) δ 2.45 (m, 4H), 2.65 (m, 4H), 2.72 (t, 2H), 2.84 (t, 2H), 3.80 (t, 2H), 4.10 (t, 2H), 4.22 (s, 1H), 5.25 (bs, 2H), 6.80 (d, 2H), 7.25 (m, 5H), 7.36 (m, 6H).

Example 3

Figure 3:
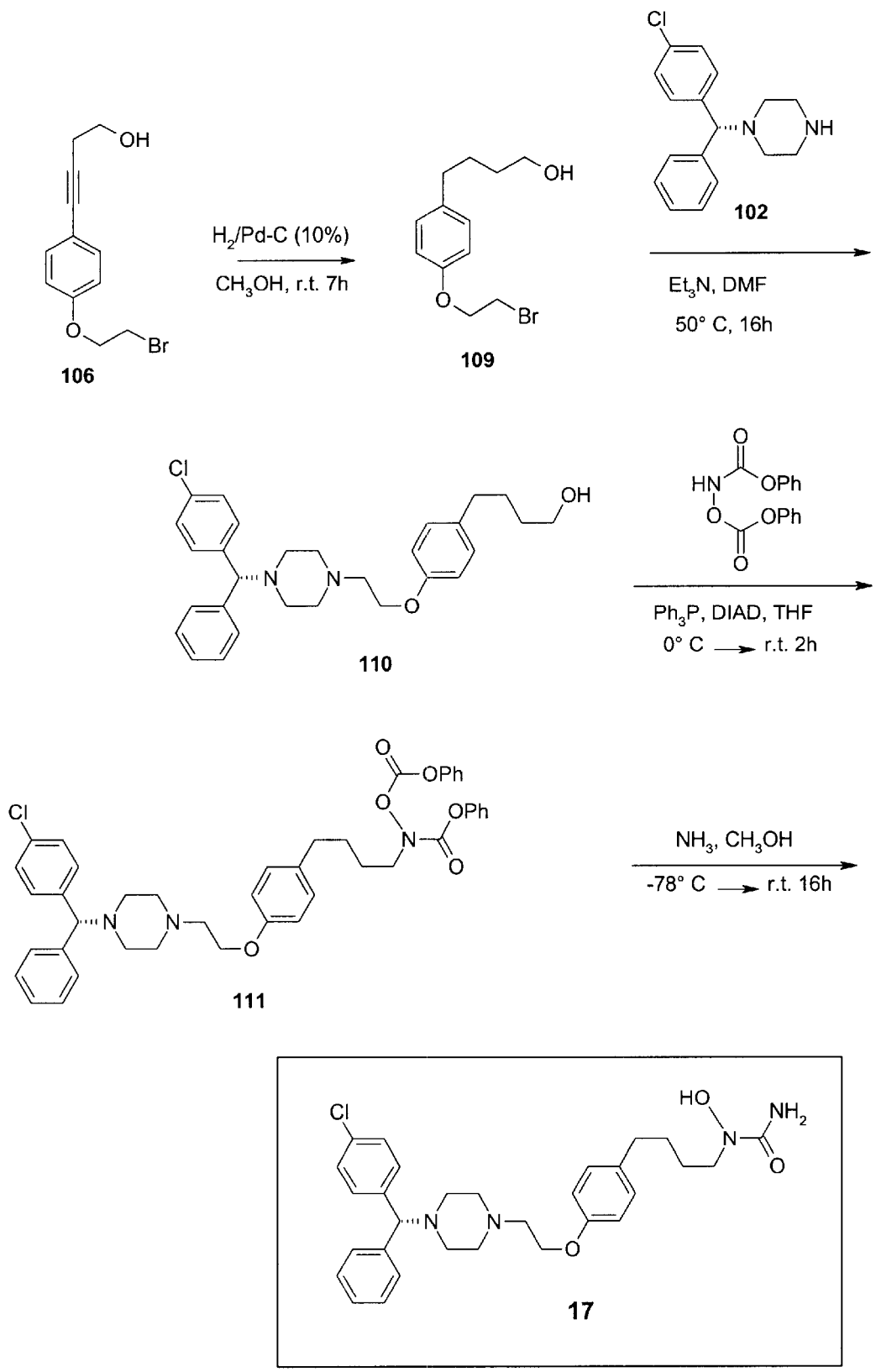
FIG. 3 displays the synthesis of compound 17.
Figure 4:
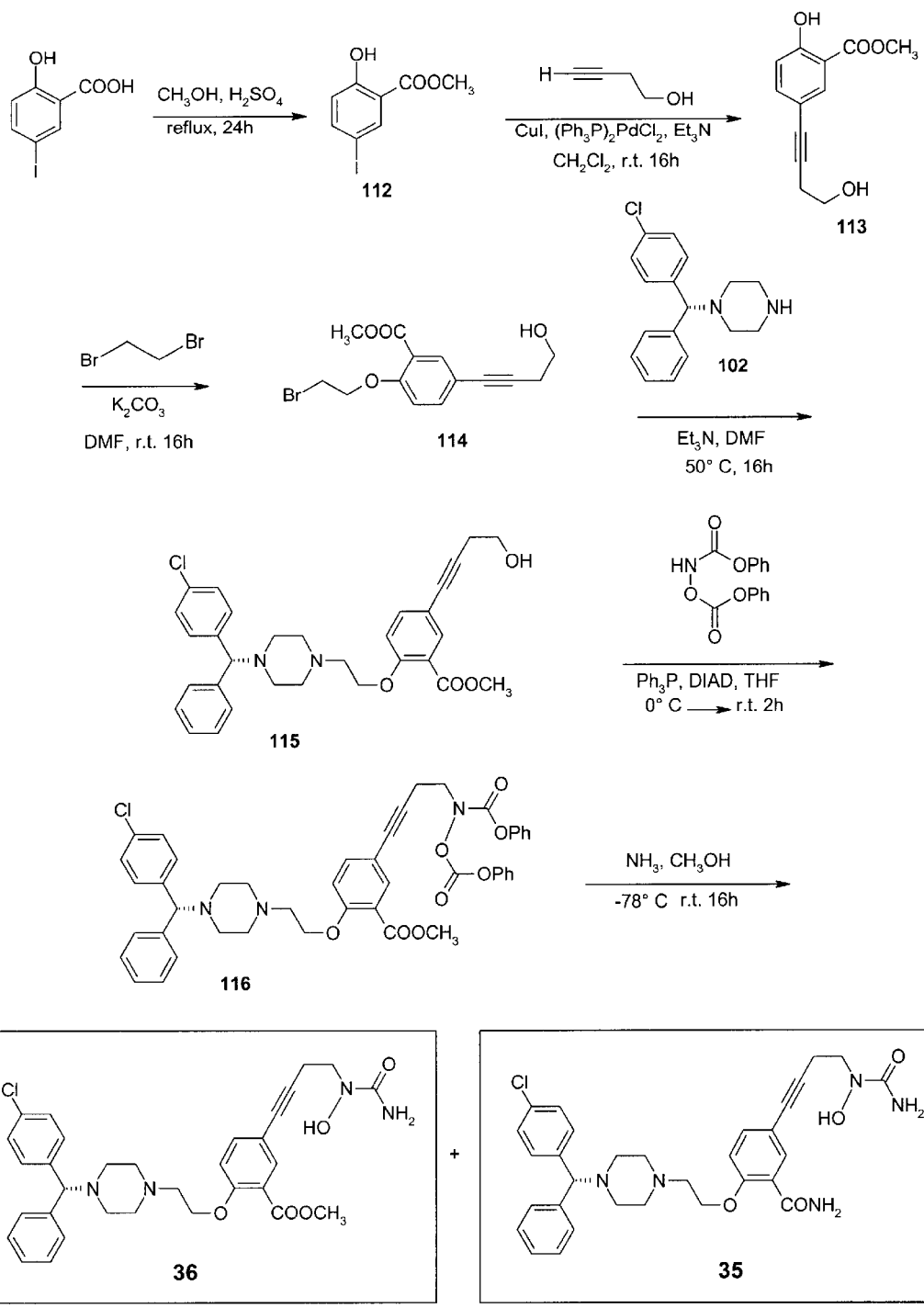
FIG. 4 displays the synthesis of compound 35 and 36.

Preparation of N-{4-[4-(2-{4-[(1R)(4-Chlorophenyl)phenylmethyl]piperazinyl}ethoxy)phenyl]butyl}-amino-N-hydroxyamide (Compound 17, FIG. 3)

4-[4-(2-Bromoethoxy)phenyl]butan-1-ol (Compound 109)

A solution of 106 (1.3 g, 4.83 mmol) in methanol (15 mL) was hydrogenated over 10% palladium on charcoal (130 mg) at balloon pressure for 7 hours. The catalyst was filtered off and the filtrate was evaporated to give 109 (1.31 g, 99.2%): ¹H NMR (CDCl₃) δ 1.65 (m, 4H), 2.60 (t, 2H), 3.66 (m, 4H), 4.28 (m, 2H), 6.83 (d, 2H), 7.10 (d, 2H).

4-{4-[2-(4-((1R)(4-Chlorophenyl)phenylmethyl)piperazinyl)ethoxy]phenyl}butan-1-ol (Compound 110)

To a solution of 109 (1.3 g, 4.76 mmol) and [(1R)(4-chlorophenyl)phenylmethyl]piperazine (102) (1.39 g, 4.86 mmol) in DMF (12 mL) was added triethylamine (762.3 mg, 7.55 mmol). The reaction was stirred at 50° C. for 16 hours, water was added, and the reaction was extracted with dichloromethane. The organic layer was washed with water and brine, dried over magnesium sulfate, filtered, and evaporated to an oil, which was purified by flash column chromatography (silica gel, 1:1 hexane/ethyl acetate) to yield 110 (2.42 g, 104%): $^1$H NMR (CDCl$_3$) δ 1.65 (m, 4H), 2.45 (m, 4H), 2.62 (m, 6H), 2.81 (t, 2H), 3.66 (t, 2H), 4.08 (t, 2H), 4.21 (s, 1H), 6.81 (d, 2H), 7.08 (d, 2H), 7.25 (m, 4H), 7.36 (m, 5H), 8.02 (bs, 1H).

N-{4-[4-(2-(4-((1R)(4-Chlorophenyl)phenylmethyl)piperazinyl)ethoxy)phenyl]butan-1-ol}phenoxycarbonylaminophenoxyformate (Compound 111)

To a stirred solution of 110 (1.5 g, 3.14 mmol), phenoxycarbonylaminophenoxyformate (1.05 g, 3.85 mmol) and triphenylphosphine (938.0 mg, 3.58 mmol) in THF (35 mL) at 0° C. was added diisopropylazodicarboxylate (724.0 mg, 3.58 mmol). After addition, the reaction was warmed to room temperature and stirred at room temperature for 2 hours. The solvent was evaporated and the residue was purified by flash column chromatography (silica gel, 2:1 hexane/ethyl acetate) to give 111 (1.58 g, 68.7%).

N-{4-[4-(2-{4-[(1R)(4-Chlorophenyl)phenylmethyl]piperazinyl}ethoxy)phenyl]butyl}-amino-N-hydroxyamide (Compound 17)

In a screw top vessel was placed a solution of 111 (1.58 g, 2.16 mmol) in methanol (50 mL) and cooled to −78° C. in a dry ice-acetone bath. To this vessel was added liquid ammonia (6 mL) and sealed. The dry ice-acetone bath was then removed and the reaction was stirred at room temperature for 16 hours. The reaction was cooled again in a dry ice-acetone bath and the pressure was released. The vessel was opened and the solvent was evaporated. Compound 17 was separated by flash column chromatography (silica gel, 19:1 CH$_2$Cl$_2$/CH$_3$OH) and further purified by recrystallization using ethyl acetate-hexane as a solvent (550 mg, 47.4%): $^1$H NMR (CDCl$_3$) δ 1.60 (m, 4H), 2.44 (m, 4H), 2.52 (t, 2H), 2.67 (m, 4H), 2.83 (t, 2H), 3.48 (t, 2H), 4.08 (t, 2H), 4.21 (s, 1H), 6.78 (d, 2H), 7.04 (d, 2H), 7.25 (m, 4H), 7.35 (m, 5H).

Example 4

Figure 5:
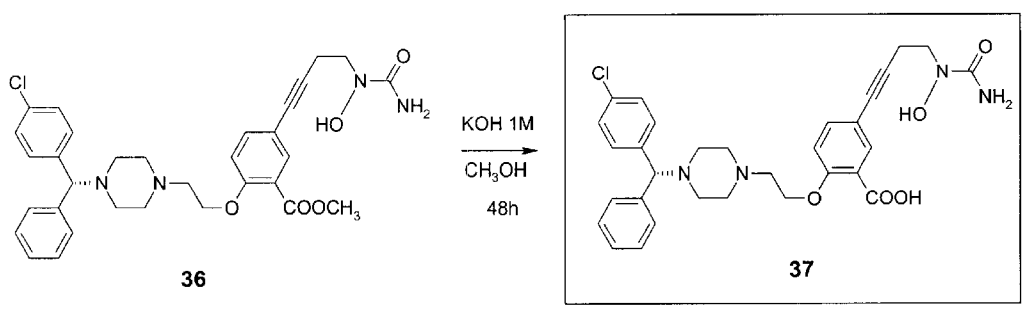
FIG. 5 displays the synthesis of compound 37.

Preparation of Methyl-2-(2-{4-[(1R)(4-chlorophenyl)phenylmethyl]piperazinyl}ethoxy)-5-[4-(aminohydroxycarbonylamino)but-1-ynyl]benzoate (Compound 36, FIG. 4), 2-(2-{4-[(1R)(4-Chlorophenyl)phenylmethyl]piperazinyl}ethoxy)-5-[4-(aminohydroxcarbonylamino)but-1-ynyl]benzamide (Compound 35, FIG. 4), and 2-(2-{4-[(1R)(4-Chlorophenyl)phenylmethyl]piperazinyl}ethoxy)-5-[4-(aminohydroxycarbonylamino)but-1-ynyl]benzoic Acid (Compound 37, FIG. 5)

4-iodophenol, Methyl Acetate (Compound 112)

To a solution of 5-iodosalicylic acid (5.0 g, 18.94 mmol) in methanol (100 mL) was added a few drops of sulfuric acid. The reaction was stirred at reflux for 24 hours. The reaction solvent (methanol) was evaporated to small volume and water was added and extracted with dichloromethane. The organic layer was washed with 10% NaHCO$_3$ solution, water and brine, dried over magnesium sulfate, filtered and evaporated to give the title compound (3.5 g, 66.5%): $^1$H NMR (CDCl$_3$) δ 3.96 (s, 3H), 6.78 (d, 1H), 7.70 (dd, 1H), 8.12 (d, 1H).

Methyl 2-Hydroxy-5-(4-hydroxybut-1-ynyl)benzoate (Compound 113)

To a mixture of 112 (2.0 g, 7.19 mmol), 3-butyn-1-ol (655.2 mg, 9.35 mmol), dichlorobis(triphenylphosphine) palladium(II) (1.0 g, 1.42 mmol) and cuprous iodide (276.3 mg, 1.45 mmol) was added triethylamine (40 mL). The reaction was stirred at room temperature for 16 hours. The solvent was evaporated and the residue was purified by flash column chromatography (silica gel, 2:1 hexane/ethyl acetate) to yield 113 (1.6 g, 101.3%): $^1$H NMR (CDCl$_3$) δ 2.68 (t, 2H), 3.81 (m, 2H), 3.96 (s, 3H), 6.92 (d, 1H), 7.50 (dd, 1H), 7.93 (d, 1H).

Methyl 2-(2-Bromoethoxy)-5-(4-hydroxybut-1-ynyl)benzoate (Compound 114)

To a solution of 113 (1.6 g, 7.27 mmol) in DMF (8 mL) was added potassium carbonate (1.51 g, 10.91 mmol). The reaction was stirred at room temperature for 30 minutes and then 1,2-dibromoethane (5.47 g, 29.09 mmol) was added. The reaction was stirred at room temperature for additional 16 hours and then quenched with water and extracted with dichloromethane. The organic layer was washed with water and brine, evaporated to yield an oil which was purified by flash column chromatography (silica gel, 2:1 hexane/ethyl acetate) to yield 114 (710 mg, 29.8%): $^1$H NMR (CDCl$_3$) δ 2.70 (t, 2H), 3.68 (t, 2H), 3.82 (t, 2H), 3.90 (s, 3H), 4.35 (t, 2H), 6.90 (d, 1H), 7.50 (dd, 1H), 7.88 (d, 1H).

Methyl 2-(2-{4-[(1R)(4-Chlorophenyl)phenylmethyl]piperazinyl}ethoxy)-5-(4-hydroxybut-1-ynyl)benzoate (Compound 115)

To a solution of 114 (300.0 mg, 0.92 mmol), [(1R)(4-chlorophenyl)phenylmethyl]piperazine (102) (262.4 mg, 0.92 mmol) in DMF (2 mL) was added triethylamine (139.0 mg, 1.38 mmol). The reaction was stirred at 50° C. for 20 hours, water was added, and the reaction was extracted with dichloromethane. The organic layer was washed with water and brine, dried over magnesium sulfate, filtered and evaporated to an oil which was purified by flash column chromatography (silica gel, ethyl acetate) to yield 115 (510 mg, 102.4%): $^1$H NMR (CDCl$_3$) δ 2.44 (m, 4H), 2.68 (m, 6H), 2.90 (m, 2H), 3.81 (t, 2H), 3.84 (s, 3H), 4.08 (m, 2H), 4.21 (s, 1H), 6.90 (d, 1H), 7.25 (m, 4H), 7.38 (m, 5H), 7.49 (dd, 1H), 7.85 (d, 1H).

N-{4-[4-(2-{4-[(1R)(4-Chlorophenyl)phenylmethyl]piperazinyl}ethoxy)-3-(methoxycarbonyl)phenyl]but-3-ynyl}phenoxycarbonylamino Phenoxyformate (Compound 116)

To a stirred solution of 115 (320.0 mg, 0.60 mmol), phenoxycarbonylaminophenoxyformate (198.4 mg, 0.73 mmol) and triphenylphosphine (55.7 mg, 0.21 mmol) in THF (2 mL) at 0° C. was added diisopropylazodicarboxylate (78.2 mg, 0.68 mmol). After addition, the reaction was warmed to room temperature and stirred at room temperature for 2 hours. The solvent was evaporated and the residue was purified by flash column chromatography (silica gel, 1:1 hexane/ethyl acetate) to give 116 (350 mg, 73.9%): $^1$H NMR (CDCl$_3$) δ 2.42 (m, 4H), 2.65 (m, 6H), 2.90 (m, 2H), 3.82 (s, 3H), 4.15 (m, 4H), 4.21 (s, 1H), 6.85 (d, 1H), 7.25 (m, 8H), 7.40 (m, 12H), 7.82 (s, 1H).

Methyl 2-(2-{4-[(1R)(4-Chlorophenyl)phenylmethyl]piperazinyl}ethoxy)-5-[4-(aminohydroxycarbonylamino)but-1-ynyl]benzoate (Compound 36) and 2-(2-{4-[(1R)(4-Chlorophenyl)phenylmethyl]piperazinyl}ethoxy)-5-[4-(aminohydroxycarbonylamino)but-1-ynyl]benzamide (Compound 35)

In a screw top vessel was placed a solution of 116 (350 mg, 0.44 mmol) in methanol (20 mL) and cooled to −78° C. in a dry ice-acetone bath. To this vessel was added liquid ammonia (3 mL) and sealed. The dry ice-acetone bath was then removed and the reaction was stirred at room temperature for 16 hours. The reaction was cooled again in a dry ice-acetone bath and the pressure released. The vessel was opened and the solvent was evaporated. Compound 36 was separated by flash column chromatography (silica gel, 9:1 $CH_2Cl_2/CH_3OH$) as a white solid. The mixture of compound 35 and 36 was further purified by flash column chromatography (silica gel, 9:1 $CH_2Cl_2/CH_3OH$) to give additional compound 36 (total 31 mg) and compound 35 (containing about 5% compound 36). Compound 35 was further separated from compound 36 by recrystallization using ethyl acetate-hexane as a solvent (35 mg).

Compound 36: $^1$H NMR (CDCl$_3$) δ 2.45 (m, 4H), 2.70 (m, 6H), 2.90 (t, 2H), 3.75 (t, 2H), 3.83 (s, 3H), 4.18 (t, 2H), 4.21 (s, 1H), 5.34 (bs, 2H), 6.85 (d, 1H), 7.25 (m, 4H), 7.37 (m, 5H), 7.43 (dd, 1H), 7.80 (s, 1H).

Compound 35: $^1$H NMR (CDCl$_3$) δ 2.40 (m, 4H), 2.54 (m, 4H), 2.75 (t, 2H), 2.80 (t, 2H), 3.80 (t, 2H), 4.20 (m, 3H), 5.42 (bs, 2H), 5.80 (bs, 1H), 6.87 (d, 1H), 7.25 (m, 4H), 7.36 (m, 5H), 7.45 (dd, 1H), 8.14 (d, 1H), 8.75 (bs, 1H).

2-(2-{4-[(1R)(4-Chlorophenyl)phenylmethyl]piperazinyl}ethoxy)-5-[4-(aminohydroxycarbonylamino)but-1-ynyl]benzoic Acid (Compound 37)

In a small round-bottomed flask was placed compound 36 (30 mg, 0.05 mmol). To this flask was added 1M KOH/ $CH_3OH$ (0.30 mL, 0.30 mmol). The reaction was stirred at room temperature for 48 hours and then cooled in an ice bath. 1 M HCl/ether (0.30 mL, 0.30 mmol) was added and the mixture was purified by flash column chromatography (silica gel, 9:1 $CH_2Cl_2/CH_3OH$) to give 37 as a white solid (9 mg, 31.4%): $^1$H NMR (CD$_3$OD) δ 2.56 (m, 4H), 2.66 (t, 2H), 2.96 (m, 4H), 3.10 (t, 2H), 3.68 (t, 2H), 4.32 (t, 2H), 4.34 (s, 1H), 6.98 (d, 1H), 7.20 (d, 1H), 7.30 (m, 4H), 7.44 (m, 6H).

Example 5

Figure 7:
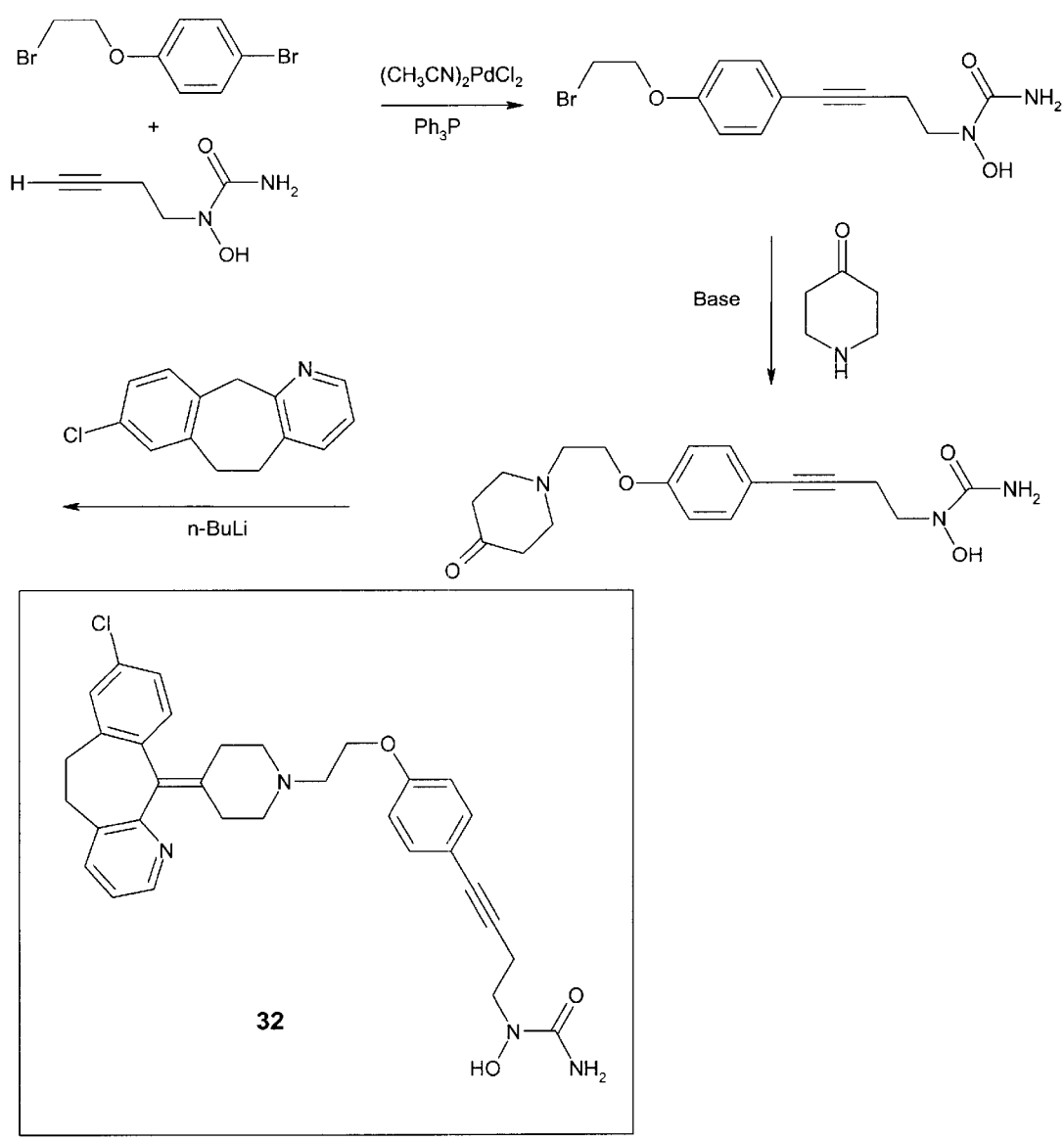
FIG. 7 displays the synthesis of compound 32.
Figure 8:
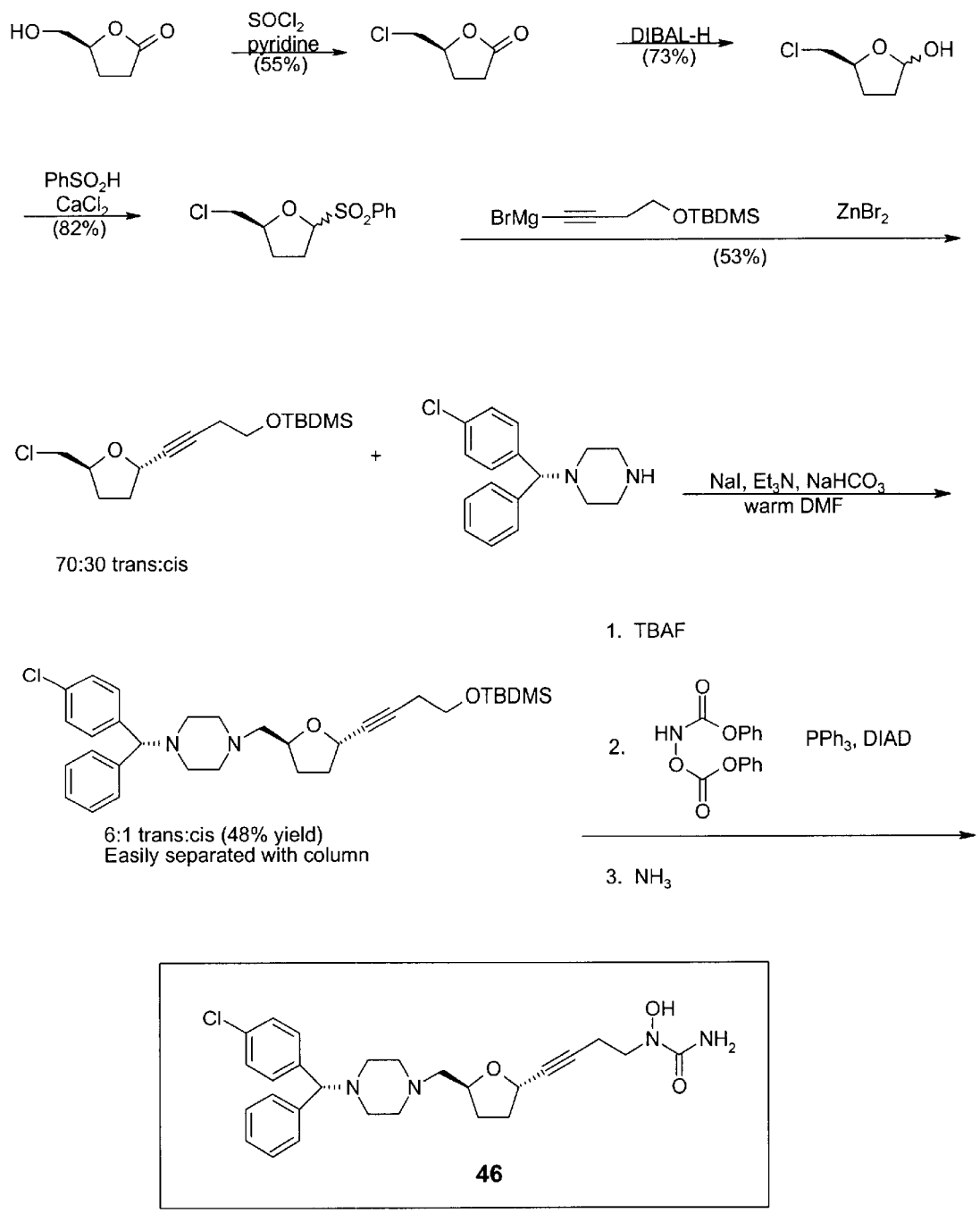
FIG. 8 displays the synthesis of compound 46.
Figure 9:
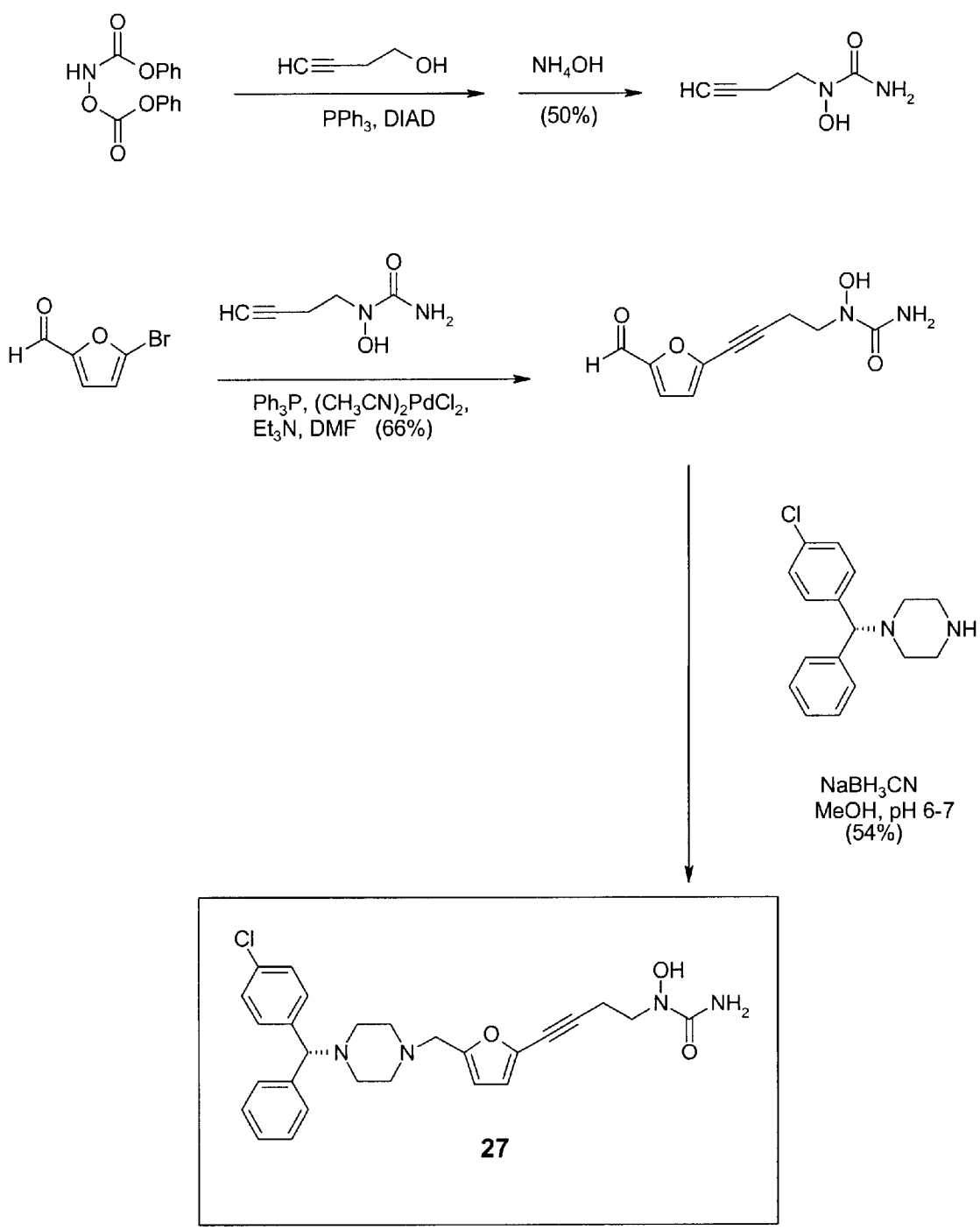
FIG. 9 displays the synthesis of compound 27.

Preparation of Amino N-{4-[4-(2-{4-(8-Chloro(5,6-dihydrobenzo[f]pyridino[2,3-b][7]annulen-11-ylidene))piperidyl}ethoxy)phenyl]but-3-ynyl}-N-hydroxyamide (Compound 32, FIG. 7)

4-(2-Bromoethoxy)-1-iodobenzene

To a stirring solution of 4-iodophenol (25 g, 110 mmol) and $K_2CO_3$ (31 g, 220 mmol) in DMF (250 mL) was added 1,2-dibromoethane (5 mL, 55 mmol) over a period of 1 hr. The solution was heated at 50° C. and stirred overnight under Ar. In order to complete the reaction additional reagents were added: 1,2-dibromoethane (20 mL, 220 mmol) and $K_2CO_3$ (6 g, 43 mmol) and the mixture was heated at 50° C. an additional 12 hours under Ar. Water was added and the reaction mixture was extracted with dichloromethane, dried over $Na_2SO_4$, filtered and the solvent evaporated under reduced pressure. The crude mixture was purified by silica gel chromatography eluted with 10% ethyl acetate in hexanes to give the title compound as a white solid (5.5 g, 17 mmol).

4-[4-(2-Bromoethoxy)phenol]but-3-yn-1-ol

To a mixture of 4-(2-Bromoethoxy)-1-iodobenzene (5.5 g, 17 mmol), 3-butyn-1-ol (1.9 mL, 25 mmol), CuI (952 mg, 5 mmol) and dichlorobis(triphenylphosphine)palladium(II) (3.5 g, 5 mmol) in dichloromethane (100 mL) was added dropwise Et$_3$N (3.5 mL, 25 mmol). The reaction was stirred overnight at room temperature under Ar. The solvent was evaporated under reduced pressure and ethyl acetate was added to dissolve the reaction mixture, which was filtered over celite to remove most of the Pd. The crude product was purified by silica gel chromatography eluted with hexane/ethyl acetate (2:1). 4 g of the title compound were obtained as a light brown solid.

4-[4-(2-{4-(8-Chloro-5,6-dihydrobenzo[f]pyridino[2,3-b][7]annulen-11-yliden)piperidyl}ethoxy)but-3-yn-1-ol 8-chloro-11-(4-piperidylidene)-5,6-dihydrobenzo[a]pyridino[2,3-d][7]annulene (2.5 g 7.75 mmol) and 4-[4-(2-bromoethoxy)phenol]but-3-yn-1-ol (2.5 g, 9.2 mmol) were disolved in dichloromethane. To this solution was added Et$_3$N (2.6 mL, 18.5 mmol) and the reaction was heated at reflux overnight under Ar. The dichloromethane was evaporated under reduced pressure. The unreacted starting materials were recovered after purification by chromatography with 10% MeOH in dichloromethane. The title compound was obtained as a white solid (1.9 g, 3.76 mmol).

Phenyl{N-{4-[4-(2-{4-(8-Chloro(5,6-dihydrobenzo[f]pyridino[2,3-b][7]annulen-11-ylidene))piperidyl}ethoxy)phenyl]but-3-ynyl}phenoxycarbonylaminooxy}formate A solution of 4-[4-(2-{4-(8-chloro-5,6-dihydrobenzo[f]pyridino[2,3-b][7]annulen-11-yliden)piperidyl}ethoxy)but-3-yn-1-ol (1.9 g, 3.76 mmol), triphenylphosphine (1.2 g, 4.7 mmol) and N,O-bis-(phenoxycarbonyl)hydroxylamine (1.3 g, 4.7 mmol) in THF (20 mL) was cooled at 0° C. with an ice bath. Diisopropylazodicarboxlate (950 mg, 4.7 mmol) was added dropwise to the stirring solution. The reaction was allowed to warm to room temperature and stir for one hour. Once the reaction was complete, the solvent was evaporated under vacuum. The product was purified by silica gel chromatography using 10% MeOH in dichloromethane. 4.5 g of the title compound (slightly impure) were obtained.

Amino-N-{4-[4-(2-{4-(8-Chloro(5,6-dihydrobenzo[f]pyridino[2,3-b][7]annulen-11-ylidene))piperidyl}ethoxy)phenyl]but-3-ynyl}-N-hydroxyamide Phenyl {N-{4-[4-(2-{4-(8-chloro(5,6-dihydrobenzo[f]pyridino[2,3-b][7]annulen-11-ylidene))piperidyl}ethoxy)phenyl]but-3-ynyl}phenoxycarbonylaminooxy}formate (4.5 g) was disolved in MeOH saturated with NH$_3$ (100 mL). The system was sealed with a rubber septum and the mixture was stirred at room temperature overnight. The solvent was evaporated under vacuum and the crude compound was purified by chromatography on silica gel, eluted with 10% MeOH saturated with NH$_3$ in dichloromethane to give the title compound, compound 32 (800 mg) [Alternatively, the reaction may be run in a pressure tube].

Example 6

Preparation of N-{4-[4-(3-{4-[(1R)(4-Chlorophenyl)phenylmethyl]piperazinyl}propoxy)phenyl]but-3-ynyl}-amino-N-hydroxyamide (Compound 52)

4-(2-Bromopropoxy)-1-iodobenzene

To a stirring solution of 4-iodophenol (15 g, 70 mmol) and $K_2CO_3$ (12.4 g, 90 mmol) in DMF (30 mL) was added 1,2-dibromopropane (7.8 mL, 90 mmol) over a period of 1 hr. The solution was heated at 50° C. and stirred overnight under Ar. Water (500 mL) was added and the reaction mixture was extracted with dichloromethane, dried over $Na_2SO_4$, filtered and the solvent evaporated under reduced pressure. Purified on silica gel chromatography, eluted with 10% ethyl acetate in hexanes to give the title compound as a white solid (10 g, 29 mmol).

4-[4-(2-Bromopropoxy)phenyl]but-3-yn-1-ol

To a solution of 4-(2-Bromopropoxy)-1-iodobenzene (10 g, 29 mmol), 3-butyn-1-ol (2.6 mL, 37 mmol), CuI (980 mg, 5.2 mmol) and dichlorobis(triphenylphosphine)palladium (II) (3.6 g, 5.2 mmol) in dichloromethane (40 mL) was added Et$_3$N (6.0 mL, 44 mmol) dropwise. The reaction was stirred overnight at room temperature under Ar. The solvent was evaporated under reduced pressure and ethyl acetate was added to dissolve the compound, the solution was filtered over celite to remove most of the Pd. The crude product was purified by silica gel chromatography, eluted with hexane/ethyl acetate (2:1). 2.6 g of the title compound were obtained as a light brown solid.

4-{4-[3-(4-((1R)(4-Chlorophenyl)phenylmethyl) piperazinyl)propoxy]phenyl}but-3-yn-1-ol

[(1R)(4-chlorophenyl)phenylmethyl]piperazine (1.6 g, 5.6 mmol) and 4-[4-(2-bromopropoxy)phenyl]but-3-yn-1-ol (2.0 g, 7.04 mmol) were dissolved in dichloromethane (10 mL). Et₃N (1 mL, 7.04 mmol) was added dropwise, the solution was heated at reflux under Ar overnight. The solvent was evaporated and the compound was purified by silica gel chromatography, eluted with ethyl acetate. 2.0 g of the title compound were obtained as a white solid.

N-{4-[4-(3-(4-((1R)(4-Chlorophenyl)phenylmethyl) piperazinyl)propoxy)phenyl]but-3-ynyl}phenoxycarbonylaminophenoxyformate A solution of 4-{4-[3-(4-((1R)(4-chlorophenyl) phenylmethyl)piperazinyl)propoxy]phenyl}but-3-yn-1-ol (1.6 g, 5.6 mmol), triphenylphosphine (1.3 g, 5.1 mmol) and N,O-bis-(phenoxycarbonyl)hydroxylamine (1.4 g, 5.1 mmol) in THF (20 mL) was cooled at 0° C. with an ice bath. Diisopropylazodicarboxlate (1.0 g, 5.1 mmol) was added dropwise to the stirring solution. Then the reaction was allowed to warm to room temperature and stir for one hour. After completion of the reaction, the solvent was evaporated under vacuum. No further purification of the compound was done.

N-{4-[4-(2-{4-[(1R)(4-Chlorophenyl)phenylmethyl] piperazinyl}propoxy)phenyl]but-3-ynyl}-amino-N-hydroxyamide (Compound 52)

N-{4-[4-(3-(4-((1R)(4-chlorophenyl)phenylmethyl) piperazinyl)propoxy)phenyl]but-3-ynyl}phenoxycarbonylaminophenoxyformate was dissolved in MeOH and added to 20 mL of condensed (dry ice/acetone) NH₃ in a pressure tube. The pressure tube was closed, allowed to warm at room temperature. After stirring overnight, the pressure was released slowly and the cap removed opening the system to the air, then the solvent was evaporated under vacuum. Purification by silica gel chromatography, eluted with 10% MeOH saturated with NH₃ in dichloromethane afforded the title compound, compound 52 (1.05 g)

Example 7

Figure 6:
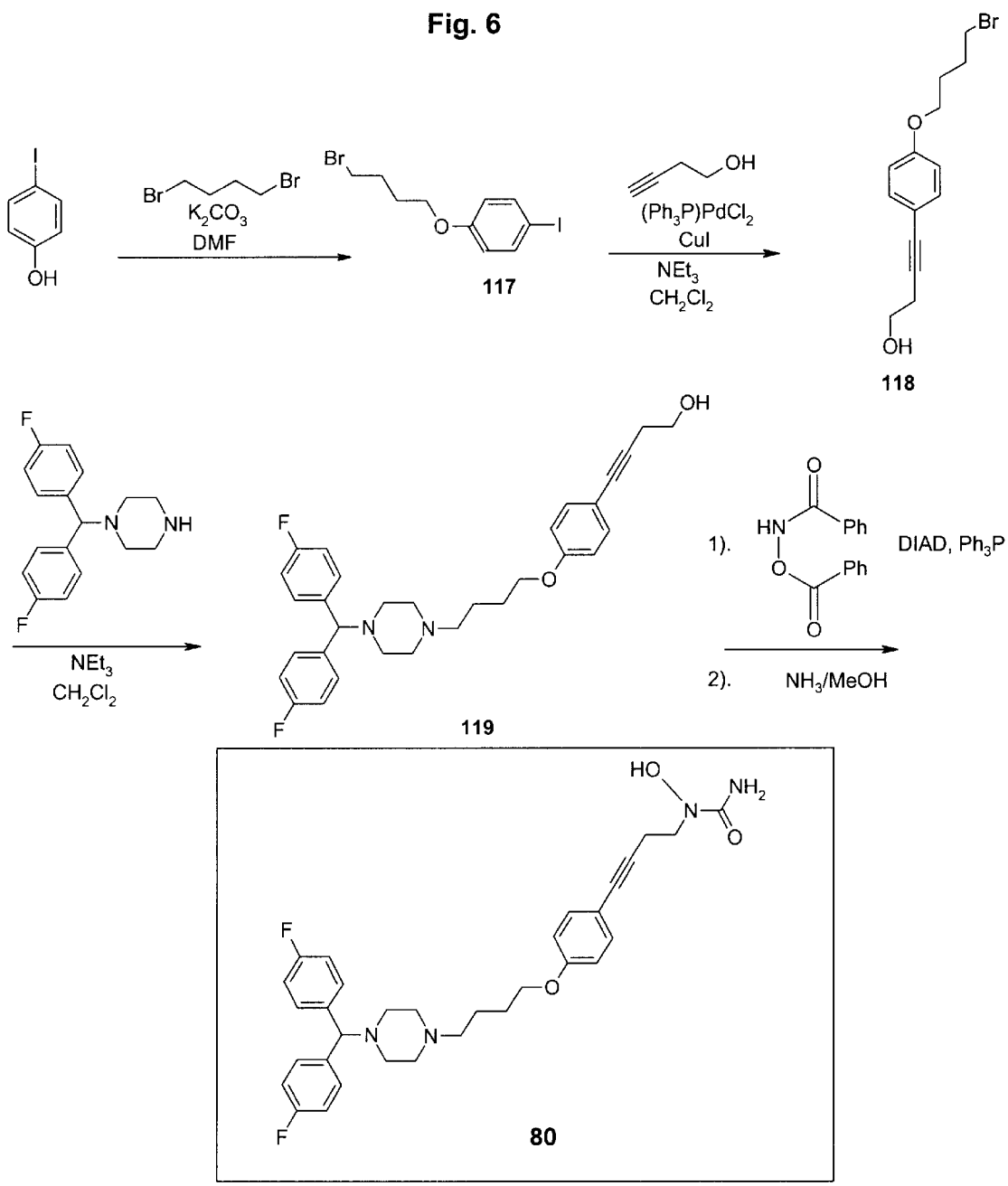
FIG. 6 displays the synthesis of compound 80.

Preparation of Amino-N-{4-[4-(4-{4-[bis(4 Fluorophenyl)methyl]piperazinyl}butoxy)phenyl] but-3-ynyl}-N-hydroxyamide (Compound 80, FIG. 6)

1-(4-bromobutoxy)-4-iodobenzene (117). To a stirring solution of 4-iodophenol (100 g, 0.5 mol) and K₂CO₃ (70 g, 0.5 mol) in DMF (400 mL) was added 1,4 dibromobutane (100 mL, 0.84 mol) over a period of 1 hr. The solution was stirred overnight at room temperature under Ar. H₂O (1000 mL) was added and the reaction mixture was extracted with CH₂Cl₂. The organic layer was then washed with 1000 mL of brine, dried over MgSO₄, concentrated to gave a white solid (100 g); ¹H NMR (CD₃Cl): δ 2.15–1.87 (m, 6H), 3.50–3.20 (m, 4H), 3.94 (t, 2H), 6.85 (d, 2H), 7.55 (d, 2H).

4-[4-(4-bromobutoxy)phenol]but-3-yn-1-ol (118). A solution of 117 (100 g, 0.3 mol), 3-butyn-1-ol (45 mL, 0.6 mol), CuI (800 mg, 4.2 mmol) and dichlorobis (triphenylphosphine) palladium(II) (2.9 g, 4.2 mmol) in dichloromethane (400 mL) was cooled at 0 C (ice bath). Et₃N (84 mL, 0.6 mol) was added dropwise while maintaining the low temperature. Then the mixture was warmed at room temperature and stirred overnight under Ar. The dichloromethane was removed under vacuum. The semi-solid obtained, was dissolved in a minimum of CH₂Cl₂ and passed over a large plug of silica gel eluting with 10% EtOAc in hexane, followed by 50% EtOAc:50% hexane. 75 g of a light tan solid were obtained; ¹H NMR (CD₃Cl) δ 2.10–1.80 (m, 4H), 2.66 (t, 2H), 3.25 (t, 1H), 3.50 (t, 2H), 3.80 (t, 2H), 3.94 (t, 2H), 6.85 (d, 2H), 7.55 (d, 2H).

Compound 119: 4-bis(4-fluorophenyl methyl piperazine (58 g, 0.2 mol) and 118 (74 g, 0.25 mol) were dissolved in CH₂Cl₂ (500 mL). To this solution was added NEt₃ (43 mL, 0.31 mol). The mixture was allowed to stir for 48 hr at room temperature under Ar. After evaporation of the solvent under vacuum, the semi-solid obtained was dissolved in a minimum amount of CH₂Cl₂ and passed over a large plug of silica gel eluting with 50% EtOAc:50% hexane, followed by EtOAc to remove the desired compound. Concentration of the solution gave an off-white foam (70 g) 90% pure; ¹H NMR (CD₃Cl) δ 1.78–1.75 (m, 6H), 2.72–2.45 (m, 12H), 3.78 (t, 2H), 3.94 (t, 2H), 4.23 (s, 1H), 6.76 (d, 2H), 6.97 (t, 4H), 7.37–7.25 (m, 6H).

Compound 80: A solution of 119 (70 g, 0.14 mol), triphenylphosphine (45 g, 0,17 mol) and N,O-bis-(phenoxycarbonyl)hydroxylamine (46 g, 0.17 mol) in THF (500 mL) was cooled at 0° C. with an ice bath. Diisopropylazodicarboxylate (34 mL, 0.17 mol) was added dropwise to the stirring solution. The ice bath was removed, the reaction was allowed to warm at room temperature and stir for 1 hr. The reaction was checked by TLC for completion. The solvent was removed under vacuum, the crude material was dissolved in 700 mL of MeOH saturated with ammonia. The mixture was stirred overnight in a round bottom flask sealed with a rubber septa. The reaction was worked up by an acid/base extraction, concentrated and passed over a large plug of silica gel (45 g), eluted with 10% MeOH in dichloromethane. The product was recrystallized with 500 mL of refluxing EtOAc, and cooled at room temperature overnight to gave 20 g pure compound; ¹H NMR (CD₃Cl) δ 1.78–1.75 (m, 6H), 2.57–2.45 (m, 10H), 2.72 (t, 2H), 3.78 (t, 2H), 3.94 (t, 2H), 4.23 (s, 1H), 5.34 (s br, 2H), 6.76 (d, 2H), 6.97 (t, 4H), 7.37–7.25 (m, 6H). The following Table II provides illustrative NMR data for the especially preferred compounds.

TABLE II

| COMPOUND # | ¹H-NMR (CDCl₃) δ (ppm) |
|---|---|
| 17 | 1.60 (m, 4H), 2.44 (m, 4H), 2.52 (t, 2H), 2.67 (m, 4H), 2.83 (t, 2H), 3.48 (t, 2H), 4.08 (t, 2H), 4.21 (s, 1H), 6.78 (d, 2H), 7.04 (d, 2H), 7.25 (m, 4H), 7.35 (m, 5H). |
| 32 | 2.20–2.95 (m, 14H), 3.35 (m, 2H), 3.72 (t, 2H), 4.05 (t, 2H), 5.62 (brs, 2H), 6.72 (d, 2H), 7.10 (m, 4H), 7.25 (d, 2H), 7.45 (d, 1H), 8.35 (d, 1H). |
| 34 | 2.45 (br d, 8H); 2.75 (t, 2H); 3.50 (s, 2H); 3.70 (t, 2H); 4.20 (s, 1H); 5.57 (br s, 2H); 6.15 (d, 1H); 6.39 (d, 1H); 6.95 (t, 4H); 7.33 (dd, 4H). |
| 35 | 2.40 (m, 4H), 2.54 (m, 4H), 2.75 (t, 2H), 2.80 (t, 2H), 3.80 (t, 2H), 4.20 (m, 3H), 5.42 (br s, 2H), 5.80 (br s, 1H), 6.87 (d, 1H), 7.25 (m, 4H), 7.36 (m, 5H), 7.45 (dd, 1H), 8.14 (d, 1H), 8.75 (br s, 1H). |
| 46 | 1.40–1.55 (m, 1H); 1.85–1.96 (m, 1H); 2.05–2.20 (m, 2H); 2.30–2.70 (m, 12H); 3.62 (ddd, 2H); 4.18 (s, 1H); 4.27 (br d, 1H); 4.63 (br t, 1H); 5.58 (br s, 2H); 7.15–7.35 (m, 9H). |
| 52 | 1.95 (m, 2H), 2.65–2.35 (m, 10H), 2.72 (t, 2H), 3.78 (t, 2H), 3.93 (t, 2H), 4.20 (s, 1H), 5.25 (brs, 2H), 6.75 (d, 2H), 7.15–7.40 (m, 11H). |

TABLE II-continued

| COMPOUND # | $^1$H-NMR (CDCl$_3$) δ (ppm) |
|---|---|
| 80 | 1.78–1.75 (m, 6H), 2.57–2.45 (m, 10H), 2.72 (t, 2H), 3.78 (t, 2H), 3.94 (t, 2H), 4.23 (s, 1H), 5.34 (s br, 2H), 6.76 (d, 2H), 6.97 (t, 4H), 7.37–7.25 (m, 6H). |

Example 8

CHO-K1 H1R Binding Assay Protocol

This assay is commonly used to measure the ability of a compound to act as a histamine H1 receptor binding ligand. As this assay employs human cloned HI receptors it can provide a good approximation of what can be expected when a compound is administered to humans.

Details of the assay procedure are as follows. CHO-K1 cells expressing the human cloned H1 receptor are grown to confluence in tissue culture dishes. Cells are harvested using D-PBS buffer (JRH Biosciences), kept at 4° C., centrifuging to pellet cells (4° C., 500 g, 10 min). The final cell pellet is homogenized and resuspended using Tris/sucrose buffer (20 mM Tris, 250 mM sucrose, pH 7.4 at 4° C.). Aliquots of the membrane preparation are stored at −70° C.

On the day of assay, the membrane preparation is thawed and centrifuged (TLA100.3 rotor, 4° C., 15 min, 23,000 rpm). The pellet is resuspended in Tris/sucrose buffer initially and then diluted further as necessary using assay buffer A (50 mM Na/KPO$_4$, 2 mM MgCl$_2$, 0.5% (w/v) BSA, pH 7.5).

For the binding assay, the membrane preparation, test compound and $^3$H-pyrilamine (2 nM final) in buffer A with 1% (v/v) DMSO final are incubated in a 96-well polypropylene plate for 3 hours at 37° C. Non-specific binding is determined in the presence of 10 µM pyrilamine. A 96-well harvester (Packard) is used to harvest the 96-well plate onto a GF/B filter plate pre-treated with 0.1% (v/v) PEI. The plate is counted in a Packard Topcounter after adding Microscint 20 (Packard) scintillation fluid. The K$_i$ for each compound at the histamine H1 receptor is then calculated from these counts. The results are displayed in Table 1, infra.

Example 9

Inhibition of LTB$_4$ Production in Human Whole Blood

This assay examines the ability of a compound to inhibit leukotriene B$_4$ production from human blood stimulated with calcium ionophore. As this production of leukotriene B$_4$ is mediated via the activation of the 5-lipoxygenase enzyme, this assay is predictive of a compound's ability to inhibit the human 5-lipoxygenase enzyme.

The procedure for the assay is as follows. Blood is drawn from normal human volunteers into tubes containing heparin. 1 ml of the heparinized blood is pipetted into a 1.5 ml polypropylene tube. To this sample is added either different concentrations of the test compound (5 µl), dissolved in DMSO or 5 µl of DMSO as a vehicle control. These samples are incubated in a water bath, at 37° C. for 15 min. 5 µl of the calcium ionophore A23187 (at a final concentration of 50 µM) is then added to each sample, which is vortexed and placed back in the water bath for 30 min. The samples are then centrifuged at 2500 rpm for 10 min. at 4° C. 50 µl of the supernatant is transferred into pre-cooled Eppendorf tubes containing 950 µl of enzyme immunoassay (EIA) buffer. A commercially available EIA kit (Cayman Chemical Co., Ann Arbor, Mich., USA) is used to subsequently measure the LTB4 production in the samples. The LTB$_4$ levels produced in the vehicle control sample is then compared to those in which the test compound has been added. From this a percent inhibition of LTB$_4$ production by each concentration of test compound is calculated and the IC$_{50}$ for inhibition of LTB$_4$ production for each test compound is determined. The results are displayed in Table 1, infra.

TABLE 1

| Cpd # | CHOH1 K$_i$ (nM) | HWB IC$_{50}$ (nM) |
|---|---|---|
| 1 | 24 | 1515 |
| 3 | 260 | 1681 |
| 5 | 23 | 2041 |
| 46 | 133 | 313 |
| 8 | 220 | 5768 |
| 9 | 12 | 4222 |
| 11 | 130 | 3626 |
| 12 | 380 | 267 |
| 80 | 27 | 78 |
| 13 | 10 | 2444 |
| 16 | 94 | 2657 |
| 87 | 58 | 251 |
| 18 | 15 | 2101 |
| 22 | 8 | 1473 |
| 23 | 10 | 287 |
| 24 | 7 | 253 |
| 26 | 4 | 1714 |
| 27 | 150 | 650 |
| 30 | 36 | 412 |
| 17 | 15 | 254 |
| 32 | 7 | 263 |
| 34 | 550 | 142 |
| 35 | 135 | 85 |
| 36 | 420 | 94 |
| 37 | 4 | 6589 |
| 40 | 120 | 122 |
| 42 | 35 | 106 |
| 52 | 6 | 105 |
| 43 | 2 | 2742 |

Example 10

Antihistaminergic Activity In Vivo

Male, Hartley guinea pigs are obtained from Charles River Labs at a body weight of 350–400 grams. Inhibition of histamine activity is measured by the method of Konzett and Rössler (*Naonyn-Schmiedebergs Arch. Exp. Path. Pharmakol.* 195, 71–74 (1940). Anaesthetized guinea pigs are subjected to artificial ventilation. The endotracheal pressure is recorded. Bronchoconstriction is induced by successive intravenous injections of histamine. The test compounds are administered orally in a 1% methocellulose suspension at set timepoints prior to the administration of histamine.

The results (Table 2) show the percent inhibition of histamine-induced bronchoconstriction by selected compounds at multiple time points post oral dosing. 50% inhibition or greater is considered significant.

TABLE 2

| Cpd # | Dose of test cpd | Time (in hours) | % inhibition |
|---|---|---|---|
| 1 | 5 mg/kg | 3 hrs | 56% |
| 12 | 2 mg/kg | 3 hrs | 62% |
| 12 | 2 mg/kg | 6 hrs | 66% |
| 87 | 2 mg/kg | 3 hrs | 66% |

TABLE 2-continued

| Cpd # | Dose of test cpd | Time (in hours) | % inhibition |
|---|---|---|---|
| 87 | 2 mg/kg | 6 hrs | 73% |
| 23 | 2 mg/kg | 3 hrs | 80% |
| 23 | 2 mg/kg | 6 hrs | 92% |
| 27 | 2 mg/kg | 3 hrs | 86% |
| 27 | 2 mg/kg | 6 hrs | 91% |
| 32 | 2 mg/kg | 3 hrs | 65% |
| 34 | 2 mg/kg | 3 hrs | 81% |
| 34 | 2 mg/kg | 6 hrs | 89% |
| 17 | 2 mg/kg | 3 hrs | 66% |
| 17 | 2 mg/kg | 6 hrs | 73% |
| 35 | 2 mg/kg | 3 hrs | 72% |
| 35 | 2 mg/kg | 6 hrs | 88% |
| 52 | 2 mg/kg | 3 hrs | 69% |
| 80 | 2 mg/kg | 3 hrs | 98% |

It can be seen from this Table that compounds of the present invention possess good activity with regard to their ability to inhibit histamine-induced bronchoconstriction. Furthermore, several of the compounds administered at a single dose possess antihistaminergic activity of long duration. For example, 27, at a dose of 2 mg/kg, still inhibits histamine-induced bronchoconstriction by 91% at 6 hours post oral dosing.

These experiments also indicate that the compounds tested are orally bioavailable.

Example 11

5-Lipoxygenase Inhibitory Activity In Vivo

Male, Hartley guinea pigs are obtained from Charles River Labs at a body weight of 350–400 grams. Compounds are prepared at a volume of [1–2 mg/ml] in 1% methocellulose for oral dosing. Animals are separated into groups of five (5). Each assay includes a control group dosed with vehicle. Each group of animals is dosed with either vehicle or compound by oral gavage. Animals are allowed to rest for one, three, or six hours after dosing. Control animals are allowed to rest for three hours. At the appropriate times, the animals are anesthetized with Urethane at 1.5 g/kg, ip. Blood is drawn into a heparinized syringe via cardiac puncture.

Blood (0.5 ml) is aliquoted into separately-labeled 1.5 ml eppendorf tubes. Each sample is loaded with 5 μl of [15 mM] Arachidonic Acid, and placed in a 37° C. water bath for five minutes. After five minutes, the blood is stimulated with 5 μl of [5 mM] A23187 (Calcium Ionophore) and retained in the water bath for an additional 30 minutes. After the thirty minutes, the blood samples are removed from the water bath and centrifuged at 14,000 rpm for 2 minutes. Plasma is diluted to EIA buffer and an EIA is performed following manufacturer instructions (Cayman Chemical Co., Ann Arbor, Mich., USA).

The results (Table 3) show the percent inhibition of 5-lipoxygenase by selected compounds at multiple time points post oral dosing. 50% inhibition or greater is considered significant.

TABLE 3

| Cpd # | Dose | Time in hours | % inhibition |
|---|---|---|---|
| 1 | 2 mg/kg | 1 hour | 62% |
| 12 | 2 mg/kg | 6 hours | 80% |
| 87 | 2 mg/kg | 1 hour | 70% |
| 87 | 2 mg/kg | 6 hours | 94% |
| 23 | 2 mg/kg | 1 hour | 80% |
| 27 | 2 mg/kg | 1 hour | 88% |
| 32 | 2 mg/kg | 1 hour | 88% |
| 17 | 2 mg/kg | 3 hours | 70% |
| 17 | 2 mg/kg | 6 hours | 94% |
| 35 | 2 mg/kg | 1 hour | 87% |
| 35 | 2 mg/kg | 3 hours | 97% |
| 52 | 2 mg/kg | 3 hours | 61% |
| 80 | 2 mg/kg | 3 hours | 73% |
| 80 | 2 mg/kg | 6 hours | 88% |
| 34 | 2 mg/kg | 3 hours | 38% |

It can be seen from this Table that compounds of the present invention possess good activity with regard to their ability to inhibit the 5-lipoxygenase enzyme. Furthermore, several of the compounds administered at a single dose possess 5-lipoxygenase inhibitory activity of long duration. For example, 87 at a dose of 2 mg/kg, still inhibits 5-lipoxygenase activity by 94% at 6 hours post oral dosing.

These experiments also indicate that the compounds tested are orally bioavailable.

Example 12

Inhibition of 15-Lipoxygenase

This assay examines the ability of a compound to inhibit production of 15-hydroxy-5,8,11,13-eicosatetraeonoic acid (15-HETE) via the action of 15-lipoxygenase on arachidonic acid. 15-lipoxygenase was purified from rabbit peritoneal polymorphonuclear leukocytes. The enzyme is responsible for the conversion of arachidonic acid (via oxygenation at carbon 15 of arachidonic acid) to 15-hydroperoxy-5,8,11,13-eicosatetraenoic acid (15-HPETE), which then reduced to 15-hydroxy-5,8,11,13-eicosatetraenoic acid (15-HETE).

The procedure for the assay is as follows. Arachidonic acid is co-incubated with 15-HETE for 5 min at 37° C. in the presence or absence of different concentrations of test compound ($10^{-8}$ to $10^{-5}$ M). Production of 15-HETE in each sample is then measured by radioimmunoassay. The 15-HETE levels produced in the vehicle control sample are then compared to those in which the test compound has been added. From this a percent inhibition of 15-HETE production by each concentration of test compound is calculated and the $IC_{50}$ for inhibition of 15-HETE production for each test compound is determined. The $IC_{50}$ s (nM) are 1300, 170, 46, 61, and 110 for compounds 1, 32, 35, 52 and 80, respectively.

We claim:
1. A compound of the formula

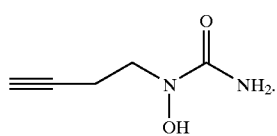

* * * * *